(12) United States Patent
Safinya et al.

(10) Patent No.: US 6,358,523 B1
(45) Date of Patent: Mar. 19, 2002

(54) MACROMOLECULE-LIPID COMPLEXES AND METHODS FOR MAKING AND REGULATING

(75) Inventors: Cyrus R. Safinya, Santa Barbara, CA (US); Joachim Oskar Raedler, Garching (DE); Ilya Koltover, Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/105,571

(22) Filed: Jun. 26, 1998

Related U.S. Application Data

(63) Continuation-in-part of application No. 08/985,625, filed on Dec. 5, 1997.
(60) Provisional application No. 60/032,163, filed on Dec. 5, 1996.

(51) Int. Cl.[7] .............................................. A61K 9/127
(52) U.S. Cl. ........................ 424/450; 424/400; 424/405; 424/484; 424/9.1
(58) Field of Search ................................ 424/400, 405, 424/450, 484, 9.1

(56) References Cited

U.S. PATENT DOCUMENTS 5,869,037 A * 2/1999 Crystal et al.
5,928,944 A * 7/1999 Seth et al.

OTHER PUBLICATIONS

Lipowski, R., "The Conformation of Membranes," *Nature*, Feb. 1991, 349:475–81. (Exhibit 1).
Walker, S. et al., "Encapsulation of Bilayer Vesicles by Self Assembly," *Nature*, May 1997, 387:61–4. (Exhibit 2).
Lasic, D., "Liposomes Within Liposomes," *Nature*, May 1997, 387:26–7. (Exhibit 3).
Raedler, J. et al., "Structure of DNA–Cationic Liposome Complexes: DNA Intercalation in Multilamellar Membranes in Distinct Interhelical Packing Regimes," *Science*, Feb. 1997, 275:810–4. (Exhibit 4).
Evans, E. A. and V. A. Parsegian, "Thermal–mechanical Fluctuations Enhance Repulsion Between Bimolecular Layers," *Proc. Natl. Acad. Sci. USA*, Oct. 1986, 83:7132–6. (Exhibit 5).
Kamien, Randall D. and David R. Nelson, "Defects in Chiral Columnar Phases: Tilt–grain Boundaries and Iterated Moire Maps," *Physical Review E*, Jan. 1996, 53(1):650–66. (Exhibit 6).
Safinya, Cyrus R. et al., "Steric Interaction in a Model Multimembrane System: A Synchrotron X–Ray Study," *Physical Review Letters*, Nov. 24, 1986, 57(21):2718–21. (Exhibit 7).
Helfrich W., "Steric Interaction of Fluid Membranes in Multilayer Systems," *Z. Naturforsch*, 1978, 33:305–15. (Exhibit 8).
Selinger, Jonathan V. and Robijin F. Bruinsma, "Hexagonal and Nematic Phases of Chains. I. Correlation Functions," *Physical Review A*, Mar. 15, 1991, 43(6):2910–21. (Exhibit 9).

(List continued on next page.)

Primary Examiner—Thurman K. Page
Assistant Examiner—P. E. McQueeney
(74) Attorney, Agent, or Firm—Mandel & Adriano

(57) ABSTRACT

The invention provides novel compositions involving macromolecule-lipid complexes and methods for making them. These compositions and methods of the invention are significant improvements in the field of macromolecule-lipid complex processing, macromolecule targeting and delivery to various biological systems.

31 Claims, 16 Drawing Sheets

OTHER PUBLICATIONS

Boltenhagen, Ph. et al., "Focal Conic Domains With Positive Gaussian Curvature and Saddle–splay Rigidity of Smectic Lα Phases," *Physical Review A,* Aug. 15, 1992, 46(4):R1743–6. (Exhibit 10).

Podgornik, Rudi et al., "The Action of Interhelical Forces on the Organization of DNA Double Helices: Fluctuation–Enhanced Decay of Electrostatic Double–Layer and Hydration Forces," *Macromolecules,* 1989, 22:1780–6. (Exhibit 11).

Safinya, Cyrus R., "Rigid Fluctuating Surfaces: A Series of Synchrotron X–ray Scattering Studies of Interacting Stacked Membranes," *Phase Transitions in Soft Condensed Matter,* Tormod Riste and Davud Sherrington, ed., Plenum Publishing Corporation, 1989, 249–70. (Exhibit 12).

Roux, D. and Cyrus R. Safinya, "A Synchrotron X–ray Study of Competing Undulation and Electrostatic Interlayer Interactions in Fluid Multimembrane Lyotropic Phases," *J. Phys. France,* 1988, 49:307–18. (Exhibit 13).

Perkins, Thomas T. et al., "Direct Observation of Tube–Like Motion of a Single Polymer Chain," *Science,* May 6, 1994, 264:819–26. (Exhibit 14).

Smith, Steven B. et al., "Direct Mechanical Measurements of the Elasticity of Single DNA Molecules by Using Magnetic Beads," *Science,* Nov. 13, 1992, 258:1122–6. (Exhibit 15).

Sternberg, Brigette et al., "New Structures in Complex Formation Between DNA and Cationic Liposomes Visualized by Freeze–Fracture Electron Microscopy," *FEBS Letters,* 1994, 356:361–6. (Exhibit 16).

Gustafsson, Jones et al., "Complexes Between Cationic Liposomes and DNA Visualized by Cryo–TEM," *Biochimica et Biophysica Acta,* 1995, 1235:305–12. (Exhibit 17).

Gershon, Hezi et al., "Mode of Formation and Structural Features of DNA–Cationic Liposome Complexes Used for Transfection," *Biochemistry,* 1993, 32:7143–51. (Exhibit 18).

Kenworthy, A. K. et al., "Range and Magnitude of the Steric Pressure Between Bilayers Containing Phospholipids with Covalently Attached Poly(ethylene glycol)," *Biophysical Journal,* May 1995, 68:1921–36. (Exhibit 19).

Warriner, Heidi E. et al., "Lamellar Biogels: Fluid–Membrane–Based Hydrogels Containing Polymer Lipids," *Science,* Feb. 16, 1996, 271:969–73. (Exhibit 20).

Ligoure, C. et al., "Polymer Induced Phase Separation in Lyotropic Smectics," *Physical Review Letters,* Nov. 22, 1993, 71(21):3600–3. (Exhibit 21).

Sackmann, E., "Supported Membranes: Scientific and Practical Applications," *Science,* Jan. 5, 1996, 271:43–8. (Exhibit 22).

Reich, Ziv et al., "Liquid–Crystalline Mesophases of Plasmid DNA in Bacteria," *Science,* Jun. 3, 1994, 264:1460–3. (Exhibit 23).

Livolant, F. et al., "The Highly Concentrated Liquid–Crystalline Phase of DNA is Columnar Hexagonal," *Nature,* Jun. 29, 1989, 339:724–6. (Exhibit 24).

Bloomfield, Victor A., "Condensation of DNA by Multivalent Cations: Considerations on Mechanism," *Biopolymers,* 1991, 31:1471–81. (Exhibit 25).

Marshall, Eliot, "Gene Therapy's Growing Pains," *Science,* Aug. 25, 1995, 269:1050–5. (Exhibit 26).

Marshall, Eliot, "Less Hype, More Biology Needed for Gene Therapy," *Science,* Dec. 15, 1995, 270:1751. (Exhibit 27).

Lasic, D. D. and N. S. Templeton, "Liposomes in Gene Therapy," *Advanced Drug Delivery Reviews,* 1996, 20:221–66. (Exhibit 28).

Nabel, Gary J. et al., "Direct Gene Transfer with DNA–Liposome Complexes in Melanoma: Expression, Biologic Activity and Lack of Toxicity in Humans," *Proc. Natl. Acad. Sci. USA,* Dec. 1993, 90:11307–11. (Exhibit 29).

Zhu, Ning et al., "Sytemic Gene Expression After Intravenous DNA Delivery into Adult Mice," *Science,* Jul. 9, 1993, 261:209–11. (Exhibit 30).

Felgner, Phillip L. et al., "Lipofection: A Highly Efficient, Liquid–Mediated DNA–Transfection Procedure," *Proc. Natl. Acad. Sci. USA,* Nov. 1987, 84:7413–7. (Exhibit 31).

Singhal, Arun and Leaf Huang, "Gene Transfer in Mammalian Cells Using Liposomes as Carriers," *Gene Therapeutics: Methods and Applications of Direct Gene Transfer,* Jon A. Wolff, ed., Birkhauser Boston, 1994, 118–42. (Exhibit 32).

Behr, Jean Paul, "Gene Transfer with Synthetic Cationic Amphiphiles: Prospects for Gene Therapy," *Bioconjugate Chemistry,* 1994, 5:382–9. (Exhibit 33).

Felgner, P. L. and G. Rhodes, "Gene Therapeutics," *Nature,* 349:351–2. (Exhibit 34).

Mulligan, Richard C., "The Basic Science of Gene Therapy," *Science,* May 14, 1993, 260:926–32. (Exhibit 35).

Crystal, Ronald G., "Transfer of Genes to Humans: Early Lessons and Obstacles to Success," *Science,* Oct. 20, 1995, 270:404–10 (Exhibit 36).

Dan, Nily, "Multilammelar Structures of DNA Complexes with Cationic Liposomes," *Biophys. J.* 1997. (Exhibit 37).

Manning, Gerald S., "Limiting Laws and Counterion Condensation in Polyelectrolyte Solutions I. Colligative Properties," *The Journal of Chemical Physics,* Aug. 1, 1969, 51(3):924–33. (Exhibit 38).

\* cited by examiner

FIG. 3A
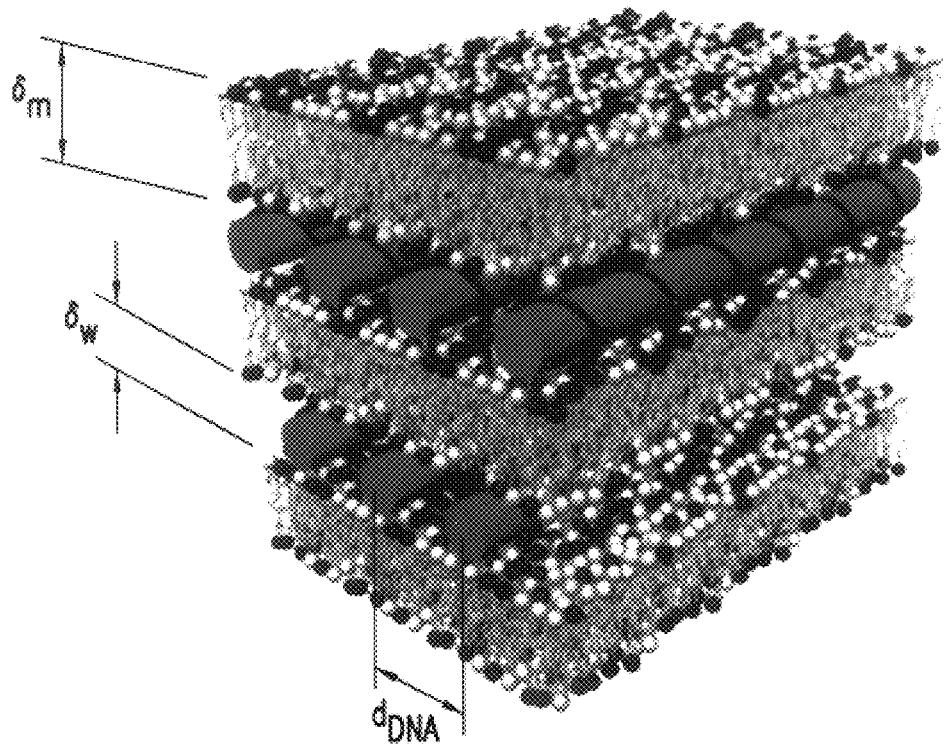
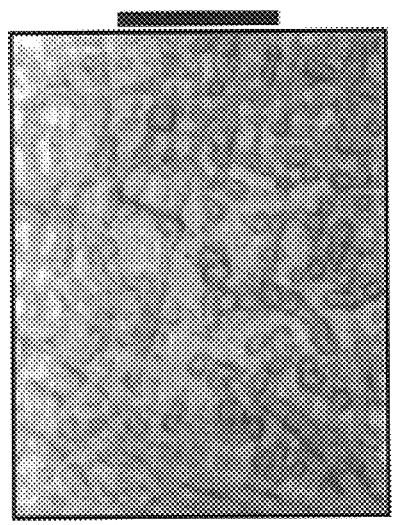
FIG. 3B
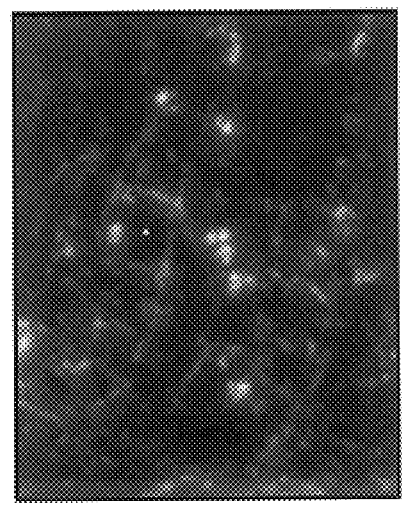
FIG. 3C

MACROMOLECULE-LIPID COMPLEXES AND METHODS FOR MAKING AND REGULATING

This application is a continuation of par U.S. Ser. No. 08/985,625, filed Dec. 5, 1997, which claims the priority of U.S. Ser. No. 60/032,163, filed Dec. 5, 1996.

This invention was made with Government support under NSF grants DMR-9624091 and DMR-9632716. The Government has certain rights in this invention.

Throughout this application various publications are referenced. The disclosures of these publications in their entireties are hereby incorporated by reference into this application in order to more fully describe the state of the art to which this invention pertains.

BACKGROUND OF THE INVENTION

Conventional macromolecule delivery and release technologies, which in the past have concentrated on improvements in mechanical devices such as implants or pumps to achieve more targeted and sustained releases of drugs, is now advancing on a microscopic and even molecular level. Recombinant technology has produced a variety of new potential therapeutics in the form of nucleic acids, proteins and peptides and these successes have driven the search for newer and more flexible macromolecule delivery and targeting methods and systems.

Microencapsulation of different molecules within biodegradable polymers and lipid complexes has achieved successes in improving the targeting and delivery of a variety of molecules including nucleic acids and various chemotherapeutic agents. For example, lipid complexes are currently used as delivery vehicles for a number of molecules where sustained release or target release to specific biological sites is desired. In the case of nucleic acids, charged nucleic acid-lipid complexes are utilized to enhance transfection efficiencies in somatic gene transfer by facilitating the attachment of nucleic acids to the targeted cells.

Success in somatic gene therapy depends on the efficient transfer and expression of extracellular DNA to the nucleus of eucaryotic cells, with the aim of replacing a defective or adding a missing gene (1). Viral-based carriers of DNA are presently the most common method of gene delivery, but there has been a tremendous activity in developing synthetic nonviral vectors. In particular, cationic liposomes (CLs), in which the overall positive charge of the cationic liposome-DNA (CL-DNA) complex enhances transfection by attaching to anionic animal cells, have shown gene expression in vivo in targeted organs, and human clinical protocols are ongoing (2–4). Cationic liposome transfer vectors exhibit low toxicity, nonimmunogenicity, and ease of production, but their mechanism of action remains largely unknown with transfection efficiencies varying by up to a factor of 100 in different cell lines (2–6).

This unpredictability, which is ubiquitous in gene therapy (7) and in particular in synthetic systems, may be attributed to a lack of knowledge regarding the interactions between DNA and CLs and the resulting structures of CL-DNA complexes. DNA membrane interactions might also provide clues for the relevant molecular forces in the packing of DNA in chromosomes and viral capsids. Studies show regular DNA condensed morphologies induced by multivalent cations (8) and liquid-crystalline (LC) phases at high concentrations of DNA both in-vitro (9) and in-vivo in bacteria (10). More broadly, the nature of structures and interactions between membranes and polymers, either adsorbed (11) or tethered to the membranes (12), is currently an active area of research.

Felgner et al. (3) originally proposed a "bead-on-string" structure of the CL-DNA complexes picturing the DNA strand decorated with distinctly attached liposomes. Electron microscopy (EM) studies have reported on a variety of structures including string-like structures and indications of fusion of liposomes in metal-shadowing EM (13), oligolamellar structures in cryo-TEM (14), and tube-like images possibly depicting lipid bilayer-covered DNA observed in freeze-fracture EM (15).

A variety of modifications of the lipid membranes have been attempted with limited success, including polymerizing or crosslinking the molecules in the bilayer to enhance stability and reduce permeation rates, and incorporating polymers into the bilayer to reduce clearance by macrophages in the bloodstream. While these modifications have proved beneficial, without means to overcome the inherent unpredictability of these complexes by controlling crucial factors such as lipid membrane thickness and the intermolecular spacing of the encapsulated molecules, the use of these molecules is severely limited. The present invention is directed to overcoming this limitation.

SUMMARY OF THE INVENTION

The invention provides novel compositions involving macromolecule-lipid complexes and methods for making them. These compositions and methods of the invention are significant improvements in the field of macromolecule-lipid complex synthesis, macromolecule targeting and delivery to various biological systems.

The present invention provides methods for making macromolecule-lipid complexes and methods for controlling components of the macromolecule-lipid complexes such as the membrane thickness and intermolecular spacing of the complex constituents.

In one embodiment for making macromolecule-lipid complexes, the method comprises mixing a lipid combination (e.g., a neutral lipid and a charged lipid) in a sufficient amount with a macromolecule so as to form a complex with specific geometric and charge qualities. By varying the relative amounts of (1) the charged and neutral lipids, (2) the weight amount and/or the macromolecule and (3) the assembly solution, conditions distinct complexes can be generated having desired isoelectric point or charged states.

By utilizing this process for controlling both the exterior lipid structure and interior macromolecular ordering, an extremely versatile molecular targeting and delivery system can be developed for a variety of applications. The invention has applications in the numerous methods which utilize lipids and various macromolecules such as gene therapy, nucleic acid based vaccine development and peptide and protein delivery.

BRIEF DESCRIPTION OF THE FIGURES

FIG. 3(A) is a schematic picture of the local arrangement in the interior of lipid-DNA complexes.

FIG. 3(B) is a micrograph of the DNA-lipid condensates under bright light.

FIG. 3(C) is a micrograph of DNA-lipid condensates under crossed polarizers.

DETAILED DESCRIPTION OF THE INVENTION

Definitions

As used in this application, the following words or phrases have the meanings specified.

As used herein, the term "surfactant" means any of various substances that are surface-active (Handbook of Lipids Research Book #4, Physical Chemistry of Lipids for Alkanes & Phospholipid, Plenum Press, London, Donald N. Small, Editor, 1988).

As used herein, the term "lipid" means any surfactant both biologically and non-biologically derived.

As used herein, the term "lipid combination" means any mixture of two or more lipids.

As used herein, the term "sufficient amount" means a concentration of a given component that is determined to be adequate to produce the desired effect or characteristic.

As used herein, the term "making" means constructing in a systematic manner.

As used herein, the term "complex" means a substance composed of two or more molecules, components, or parts.

As used herein, the term "isoelectric point state" means the set of conditions under which the electric charge of the complex is approximately zero.

As used herein, the term "negative state" means the set of conditions under which the electric charge of the complex has a net negative charge.

As used herein, the term "positive state" means the set of conditions under which the electric charge of the complex has a net positive charge.

As used herein, the term "charged state" means the set of conditions under which the electric charge of the complex. has some net charge or zero charge.

As used herein, the term "the macromolecule interaxial distance ($d_M$)" means the perpendicular distance between the cylinder axis of neighboring macromolecules or the average distance between macromolecules.

As used herein, the term "membrane thickness of the lipid combination ($\delta_m$)" means the thickness of a bilayer of lipid molecule made up of a particular lipid combination.

As used herein, the term "macromolecule area ($A_M$)" means the cross section area of the macromolecule.

As used herein, the term "area per lipid chain ($A_L$)" means the cross section area of the lipid chain.

As used herein, "macromolecule density ($\rho M$)" means the density of the macromolecule.

As used herein "lipid density ($\rho L$)" means the density of the lipid combination.

Figure 14:
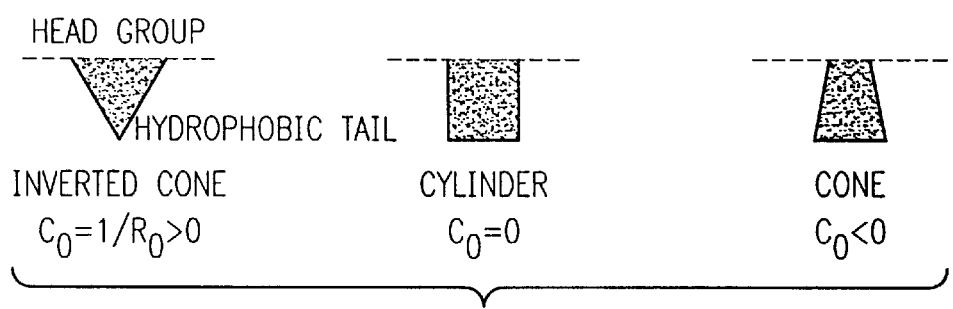
FIG. 14 is a schematic of three common shapes of lipid molecules (surfactants).

As used herein "inverted hexagonal complex phase" means the phase wherein the lipid combination forms a monolayer around the macromolecule (i.e., with lipid tails pointing outward); thereby creating a lipid monolayer macromolecule tube which then assembles into a hexagonal lattice. Also referred to herein as a cone shaped molecule (FIG. 14).

As used herein "regular hexagonal complex phase" means the phase wherein the lipid combination assembles into a cylindrical rod (i.e. with lipid tails pointing inward) and macromolecule attached to the outer surface of the rod; thereby creating cylindrical rods with attached macromolecules which then assemble in a hexagonal lattice. Also referred herein as an inverted cone shaped molecule (FIG. 14).

As used herein "modulating" means determining the amounts of the macromolecule and lipid combination sufficient produce a macromolecule-lipid complex having a desired structure.

As used herein "co-surfactant" is a membrane altering agent, i.e., an agent that reduces membrane rigidity or changes the spontaneous curvature of the membrane (i.e., the stiffness modulus). An example includes, but is not limited to, an alcohol. There are a wide variety of alcohols that will serve to produce a flexible membrane (e.g., in the range of $1k_BT<K<20k_BT$). Medium chain alcohols from butanol to nonanol will function in this context, with pentanol, heptanol and hexanol being preferred. Additionally, biologically derived alcohols such as geraniol will also function in this manner.

As used herein "κ" is the lipid monolayer rigidity.
As used herein "R" the radius of curvature.
As used herein "$R_o$" is the natural radius of curvature.
As used herein the natural curvature of cationic DOTAP is defined as $C_o^{DOTAP}=1/R_o^{DOTAP}=0$. This expresses the fact that membranes of pure DOTAP are known to favor the lamellar $L_\alpha$ phase.

As used herein the natural curvature of DOPE is defined as $C_o^{DOPE}=1/R_o^{DOPE}<0$. This expresses the fact that membranes of pure DOPE have a negative natural curvature and that DOPE has a larger area per 2 chains than area per head group.

As used herein $\Phi_{PE}^V$ is the volume fraction of DOPE in the lipid mixture monolayer.

As used herein the natural curvature of the monolayer mixture of DOTAP and DOPE is expressed as $C_o=1/R_o=\Phi_{PE}^V C_o^{DOPE}$.

In order that the invention herein described may be more fully understood, the following description is set forth.

Methods of the Invention

The invention provides methods for regulating the structure of a charged macromolecule-lipid complex having a selected characteristic or multiple characteristics. These characteristics include interaxial distance ($d_M$), membrane thickness of the lipid combination ($\delta_m$), macromolecule area ($A_M$), macromolecule density ($\rho_M$), lipid density ($\rho_L$), and the ratio (L/D) between the weight of the lipid combination (L) and the weight of the macromolecule (D). The benefit of being able to precisely control the micromolecular structure of macromolecule-lipid complexes is that it will be possible to tailor make specific structures which have defined chemical and biological activities. For example specific structural attributes of cationic lipid-DNA structures are known to impact transfection efficiencies in different biological systems. By being able to manipulate these structural attributes, the chance of success in somatic gene therapy, which depends on the efficient transfer and expression of extracellular DNA to the nucleus of eucaryotic cells, will be greatly improved.

The complex comprises a macromolecule and lipid combination. Preferably, both the macromolecule and lipid combination are charged. Further, the charge of the lipid combination or lipid is preferably opposite of the charge of the macromolecule.

Preferably, the lipid combination comprises a neutral lipid component and a charged lipid component. By varying the relative amount of the charged and neutral lipid, and the weight of the macromolecule, distinct complexes can be generated having selected isoelectric point or charged states. For example, the lipid combination and the macromolecule can be associated so as to form a complex in an isoelectric point state. Alternatively, the lipid combination and the macromolecule can be associated so as to form a complex in a positively charged state. Further alternatively, the lipid combination and the macromolecule can be associated so as to form a complex in a negatively charged state.

Additionally, in accordance with the practice of the invention, the ratio of the neutral lipid component relative to the charged lipid component can be 70/30, 50/50, 0/100, or 10/90. It clear that in the embodiment, wherein the ratio of the neutral lipid component relative to the charged lipid component is 0/100, a lipid combination is not used but only a single lipid component is used.

Examples of suitable macromolecules include nucleic acid molecules, peptides, proteins, polysaccharides, combinations of a protein and carbohydrate moiety and a synthetic macromolecule of non-biological origin, e.g., doped polyacetylene macromolecules (J. G. S. Cowie "Polymers Chemistry and Physics of Modern Materials", Chapter 7, (Blackie Academic & Professional Press) (1993)).

Examples of suitable neutral lipids include but are not limited to: dioleoyl phosphatidyl cholin, 1,2-dioleoyl-sn-glycero-3-phosphoethanolamine, 1,2-dicaproyl-sn-glycero-3-phosphoethanolamine, 1,2-dioctanoyl-sn-glycero-3-phosphoethanolamine, 1,2-dicapryl-sn-glycero-3-phosphoethanolamine, 1,2-dilauroyl-sn-glycero-3-phosphoethanolamine, 1,2-dimyristoyl-sn-glycero-3-phosphoethanolamine, 1,2-dipentadecanoyl-sn-glycero-3-phosphoethanolamine, 1,2-dipalmitoyl-sn-glycero-3-phosphoethanolamine, 1,2-diphytanoyl-sn-glycero-3-phosphoethanolamine, 1,2-dipalmitoleoyl-sn-glycero-3-phosphoethanolamine, 1,2-distearoyl-sn-glycero-3-phosphoethanolamine, 1,2-dipretrselinoyl-sn-glycero-3-phosphoethanolamine, 1,2-dielaidoyl-sn-glycero-3-phosphoethanolamine, 1,2-dilauroyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-docosahexaenoyl-sn-glycero-3-phosphoethanolamine, 1,2-myristoleoyl-sn-glycero-3-phosphocholine, 1,2-dimyristelaidoyl-sn-glycero-3-phosphocholine, 1,2-palmitoleoyl-sn-glycero-3-phosphocholine, 1,2-palmitelaidoyl-sn-glycero-3-phosphocholine, 1,2-petroselinoyl-sn-glycero-3-phosphocholine, 1,2-dioleoyl-sn-glycero-3-phosphocholine, 1,2-dielaidoyl-sn-glycero-3-phosphocholine, 1,2-dilinoleoyl-sn-glycero-3-phosphocholine, 1,2-linolenoyl-sn-glycero-3-phosphocholine, 1,2-eicosenoyl-sn-glycero-3-phosphocholine, 1,2-arachidonoyl-sn-glycero-3-phosphocholine, 1,2-erucoyl-sn-glycero-3-phosphocholine, 1,2-nervonoyl-sn-glycero-3-phosphocholine, 1,2-propionoyl-sn-glycero-3-phosphocholine, 1,2-butyroyl-sn-glycero-3-phosphocholine, 1,2-valeroyl-sn-glycero-3-phosphocholine, 1,2-caproyl-sn-glycero-3-phosphocholine, 1,2-heptanoyl-sn-glycero-3-phosphocholine, 1,2-capryloyl-sn-glycero-3-phosphocholine, 1,2-nonanoyl-sn-glycero-3-phosphocholine, 1,2-capryl-sn-glycero-3-phosphocholine, 1,2-undecanoyl-sn-glycero-3-phosphocholine, 1,2-lauroyl-sn-glycero-3-phosphocholine, 1,2-tridecanoyl-sn-glycero-3-phosphocholine, 1,2-myristoyl-sn-glycero-3-phosphocholine, 1,2-pentadecanoyl-sn-glycero-3-phosphocholine, 1,2-palmitoyl-sn-glycero-3-phosphocholine, 1,2-phytanoyl-sn-glycero-3-phosphocholine, 1,2-heptadecanoyl-sn-glycero-3-phosphocholine, 1,2-stearoyl-sn-glycero-3-phosphocholine, 1,2-bromostearoyl-sn-glycero-3-phosphocholine, 1,2-nonadecanoyl-sn-glycero-3-phosphocholine, 1,2-arachidoyl-sn-glycero-3-phosphocholine, 1,2-heneicosanoyl-sn-glycero-3-phosphocholine, 1,2-behenoyl-sn-glycero-3-phosphocholine, 1,2-tricosanoyl-sn-glycero-3-phosphocholine, 1,2-lignoceroyl-sn-glycero-3-phosphocholine.

Examples of suitable charged lipids include, but are not limited to, 1,2-diacyl-3-trimethylammonium-propane, 1,2-dimyristoyl-3-trimethylammonium-propane, 1,2-dipalmitoyl-3-trimethylammonium-propane, 1,2-distearoyl-3-trimethylammonium-propane, 1,2-diacyl-3-dimethylammonium-propane, 1,2-dimyristoyl-3-dimethylammonium-propane, 1,2-dipalmitoyl-3-dimethylammonium-propane, 1,2-distearoyl-3- dimethylammonium-propane, and 1,2-dioleoyl-3-dimethylammonium-propane.

In accordance with the practice of the invention, the nucleic acid molecule can be single stranded, double stranded, triple stranded or quadruple stranded. Further, the nucleic acid molecule can be DNA or RNA. The DNA or RNA can be naturally occurring or recombinantly-made. Alternatively, it can be a synthetic polynucleotide. The polynucleotides include nucleic acid molecules having non-phosphate backbones which improve binding. The macromolecule may be linear, circular, nicked circular, or supercoiled.

In one embodiment of the invention, the method comprises selecting a selected characteristic or characteristics described above and modulating one or more of the non-selected characteristics from the group so as to regulate the structure of the macromolecule-lipid complex having the selected characteristic. Preferably, modulation is effected using the formula: $dM=(L/D)(A_M\rho_M)/(\delta_m\rho_L)$. The relationship $d_M=(A_M/\rho_m)/(\delta_m/\rho_l)(L/D)$ equates the cationic charge density (e.g., due to the cationic membrane) with the anionic charge density (e.g., due to the macromolecule). Here, $\rho_M$=density of macromolecule (g/cc) and $\rho_L$=densities of membrane, $d_m$ the membrane thickness, and $A_M$ the macromolecule area.

In another embodiment of the invention, the method comprises modulating any of the characteristics (i.e., a single characteristic or multiple characteristics) associated with the charged macromolecule-lipid complex as described above so as to regulate the structure of the macromolecule-lipid complex having the selected characteristic.

The method further comprises determining amounts of the macromolecule and the lipid combination so selected which would be sufficient to achieve the selected characteristic or characteristics thereby regulating the structure of the complex. In one embodiment this can be accomplished by selecting a selected characteristic or multiple characteristics to be achieved. These characteristics are macromolecule interaxial distance ($d_M$), membrane thickness of the lipid combination ($\delta_m$), macromolecule area ($A_M$), macromolecule density ($\rho_M$), lipid density ($\rho_L$), and the ratio (L/D) between the weight of the lipid combination (L) and the weight of the macromolecule (D). Then the characteristics not selected can be modulated so as to achieve the selected characteristic. After determining the proper amounts, the method provides mixing the macromolecule with the lipid combination in the amount so determined.

For example, when the selected characteristic is a specific value of the interaxial distance of adjacent macromolecules within the macromolecule-lipid complex, the method provides selecting a charged macromolecule and lipid combination, wherein the charge of the lipid combination is opposite of the charge of the macromolecule. The amounts of the macromolecule and lipid combination sufficient to regulate the structure of the complex is then determined using the formula $d_M=(L/D)(A_M\rho_M)/(\delta_m\rho_L)$. In one example the interaxial distance is in a range between 24.5 and 60 angstroms. In another example, the interaxial distance is about 60 angstroms. By regulating the interaxial distance of adjacent macromolecules in a complex, the distance between macromolecules within the complex or phase is necessarily regulated. Therefore, this invention also encompasses methods for regulating the distance between macromolecules.

Alternatively, when the selected characteristic is a specific value for the average density of macromolecules within a macromolecule-lipid complex, the amounts of the macromolecule and lipid combination sufficient to regulate the structure of the complex is determined using the formula, $d_M=(L/D)(A_M\rho_M)/(\delta_m\rho_L)$.

Further, the macromolecule-lipid complex can be a multilamellar structure wherein the lipid combination forms alternating lipid bilayers and macromolecule monolayers. Alternatively, the macromolecule-lipid complex can form either an inverted hexagonal complex phase or a regular hexagonal complex phase. The complex, whether part of a multilamellar or hexagonal structure, comprises macromolecules associated with the lipid in an arrangement that can be regulated and controlled in accordance with the method of the invention.

In another embodiment, the lipid combination and the macromolecule are associated so as to form a complex in an isoelectric point state and the complex has macromolecules exhibiting interaxial spacing of greater than 24.5 angstroms. The resulting complex can have a charge of about zero. In another embodiment, the lipid and the macromolecule is associated so as to form a complex in an isoelectric point state, wherein the amount of the neutral lipid component relative to the charged lipid component ranges from 2 to 95 percent. The resulting complex can have a charge of about zero. Further, the lipid and the macromolecule can associate so as to form a complex in a charged state, wherein the amount of the neutral lipid component relative to the charged lipid component ranges from 55 to 95 percent. The resulting complex can have a net charge.

Additionally, the lipid combination can form a bilayer membrane to which charged macromolecules are associated, and wherein the relative amounts of the lipid components generate the lipid bilayer membrane having a thickness of between 25 and 70 angstroms. Alternatively, the lipid combination can form a bilayer membrane to which charged macromolecules are associated and wherein the relative amounts of the lipid components generate the lipid bilayer membrane having a thickness of between 41 and 60 angstroms. Further, the lipid combination can form a bilayer membrane to which charged macromolecules are associated, and wherein the relative amounts of the lipid components generate the lipid bilayer membrane having a thickness of between 32 and 48 angstroms.

Also, the lipid combination can form a monolayer membrane to which charged macromolecules are associated, and wherein the relative amounts of the lipid components generates the lipid monolayer membrane having a thickness of between 12 and 40 angstroms.

In addition to the bilayer membrane form (also referred to herein as lamellar or multilamellar), the resulting complex can form a monolayer (also referred to herein as being in a hexagonal phase, e.g. inverted hexagonal or regular hexagonal). For example, the lipid combination can form a monolayer membrane to which charged macromolecules are associated and wherein the relative amounts of the lipid components generate the lipid monolayer membrane having a thickness of between 15 and 35 angstroms. Alternatively, the lipid combination can form a monolayer membrane to which charged macromolecules are associated, wherein the relative amounts of the lipid components generate the lipid monolayer membrane having a thickness of between 16 and 30 angstroms.

The invention further provides a macromolecule-lipid complex produced by the methods of the invention described above.

In one embodiment, the resulting macromolecule-lipid complex comprises a lipid combination having a charged lipid component and a neutral lipid component; and a charged macromolecule. The charge of the lipid combination being opposite of the charge of the macromolecule. The lipid combination and the macromolecule associate thereby forming a complex in an isoelectric point state. In this state, the lipid combination forms a bilayer membrane to which the charged macromolecule is associated and the relative amounts of the neutral lipid component relative to the charged lipid component generates a lipid bilayer membrane having a thickness of between 25 and 75 angstroms.

In another embodiment, in the resulting macromolecule-lipid complex, the lipids form a bilayer membrane to which the macromolecule is associated, wherein the relative amounts of the lipid components generate a lipid bilayer membrane having a thickness of between 25 and 75 angstroms; and the conformation of the complex has macromolecules exhibiting interaxial spacing of a range between 50 and 75 angstroms.

The invention further provides a process for generating formulations which form the basis for the processing of templates (e.g., during a lithography process) and for producing molecular sieves with precise control over pore size for sizing molecules.

For example, the invention provides a process for creating a pattern on a surface (e.g., during a lithography process) using complexes having regulated structures made using the methods described above. The process comprises applying a lipid combination on the surface and applying macromolecules over the lipid combination. Alternatively, the macromolecule can be applied on the surface and the lipid combination applied over the macromolecules. The amounts of the macromolecule and lipid combination is determined by the formula: $d_M=(L/D)(A_M\rho_M)/(\delta_m\rho_L)$. Mixing the amounts so determined results in macromolecules which self assemble onto the lipid combination (or vice versa) thereby forming a complex and creating a pattern created by the complex on the surface. In one embodiment, the pattern can be used to create a mask, e.g., for lithography.

Additionally, the invention provides a process for creating a material having selected properties such as optical, mechanical, electronic, optoelectronic, or catalytic characteristics not previously realized from bulk components of the material. This process comprises applying a macromolecule-lipid complex to a surface. The complex must have a regulated structure created by the methods of the invention. The process further provides applying molecules which make up the material onto the complex, wherein the molecules self-assemble based on its interactions with the complex. The complex is then removed from the surface thereby creating the material having a selected property. The complex can be in a multilamellar, regular hexagonal phase, or inverted hexagonal phase. The resulting material can function as a molecular sieve having precise pore size. The invention further provides a molecular sieve produced by the process above.

Figure 10:
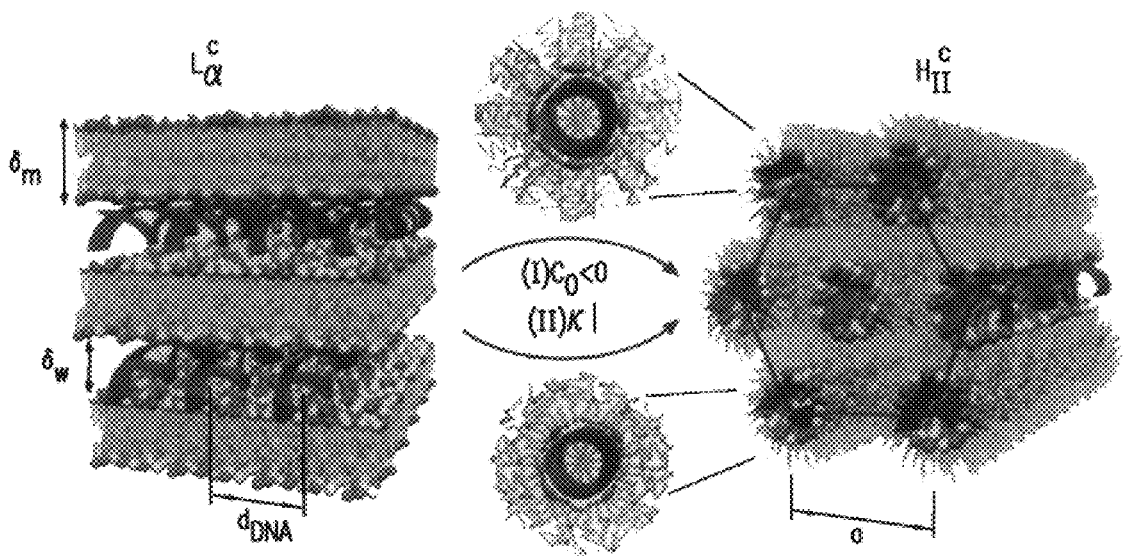
FIG. 10 is a schematic of two distinct pathways from the lamellar ($L_\alpha^C$) phase to the columnar inverted hexagonal ($H_{II}^C$) phase of cationic liposome-DNA (CL-DNA) complexes.

The invention also provides methods for creating a macromolecule-lipid complex in an hexagonal phase (also referred to herein as a regular hexagonal phase) (See pathway I of FIG. 10). In one embodiment the method comprises determining an amount of the lipid or lipid combination. This can be done by selecting a lipid or lipid combination where the sum of the products of the spontaneous curvature for each lipid and the volume fraction for each lipid is greater than zero (Biochemistry of Lipids and Membranes, edited by J. E. Vence, Benjamin Cummings Publishing Company, Menlo Park, 1985; (Israel Achvili, Intermolecular and Surface Forces, $2^{nd}$ Ed., 1991, Academic Press Limited). Further, the method provides adding a macromolecule to the lipid or lipid combination determined under sufficient conditions thereby creating the macromolecule-lipid complex in the hexagonal phase.

The invention also provides methods for creating a macromolecule-lipid complex in an inverted hexagonal phase (See pathway I of FIG. 10). In this instance, the method comprises determining an amount of the lipid or lipid combination by selecting a lipid or lipid combination where the sum of the products of the spontaneous curvature for each lipid and the volume fraction for each lipid is less than zero. Additionally, a macromolecule or macromolecules is added to the lipid or lipid combination so selected so as to create the macromolecule-lipid complex in the inverted hexagonal phase.

Additionally the invention provides methods for creating a macromolecule-lipid complex in a lamellar phase (See pathway I of FIG. 10). This method comprises determining an amount of the lipid or lipid combination by selecting a lipid or lipid combination where the sum of the products of the spontaneous curvature for each lipid and the volume fraction for each lipid is approximately zero. Additionally, a macromolecule or macromolecules can be added to the lipid or lipid combination so determined so as to create the macromolecule-lipid complex in the lamellar phase.

In accordance with the practice of the invention, the volume fraction of the lipid can be determined from FIG. 3 for each of the desired phase. Once the phase is selected, the required volume fraction to achieve that phase can be determined as demonstrated in Example 4 because the spontaneous curvature of the lipid is known or a constant.

In one embodiment of the invention, when the complex is in hexagonal or inverted hexagonal phase, the volume fraction of the lipid is greater than 0.6. In another embodiment, when the complex is in hexagonal or inverted hexagonal phase, the volume fraction of the lipid is greater than 0.7 and less than 0.85. Additionally, in one embodiment, when the complex is in lamellar phase, the volume fraction of the lipid is less than 0.4.

Additionally, the invention provides a further step to each of the invention above, namely, the step of adding a cosurfactant molecule to the complex so created. The cosurfactant molecules alters the rigidity of the lipid membrane thus allowing modifications to the membrane. Example 4 teaches this altered membrane can provide a molecule delivery system superior to those known in the art.

The present invention also provides additional embodiments for methods of making a macromolecule-lipid complex in the desired phase, e.g., lamellar, hexagonal, or inverted hexagonal phase. In one embodiment, the complex comprises a lipid or lipid combination, a macromolecule or macromolecules, and a cosurfactant or cosurfactants (See pathway II of FIG. 10).

In this embodiment, the method comprises selecting the lipid or lipid combination and macromolecule(s) appropriate for making the desired phase. This is done by determining the membrane bending rigidity of the lipid or lipid combination and macromolecule(s) (lipid/macromolecule combination). Additionally, the spontaneous curvature of the lipid/macromolecule combination is determined. One can determine the type and the amount of cosurfactant necessary to achieve the desired phase by determining the membrane bending rigidity of the lipid or lipid combination and macromolecules, the cosurfactant(s). Example 4 discloses how such a determination can be done.

Once the cosurfactant is selected, the addition of the surfactant to the lipid/macromolecule combination will result in an alteration to the membrane bending rigidity and the spontaneous curvature of the membrane is zero or non-zero.

The invention also provides macromolecule-lipid complexes produced by the method of the invention.

Additionally, the invention provides methods for transferring the macromolecule or macromolecules in the macromolecule-lipid complexes of the invention to a cell or desired surface. This comprises contacting the complex with the cell or surface under sufficient conditions so that the macromolecule or macromolecules are released from the complex thereby resulting in transfer. The chosen cosurfactant can enhance or deter the ability of the complex to transfer the macromolecule therein. The lipid or lipid combination selected also effects the transfer ability.

Also, the invention provides lubricant compositions comprising any of the macromolecule-lipid complexes of the invention and an acceptable carrier. The lubricant exhibits liquid crystalline properties. The structure of these lubricants is only weakly temperature dependent and is changed primarily by changing the composition of surfactants(e.g. lipids)/cosurfactants/macromolecules.

The lubricants are processed to be either water or oil soluble. The major phases are (1) the lamellar L$\alpha$, (2) the hexagonal H$_I$, and (3) the inverted hexagonal H$_{II}{}^C$. The L$\alpha$ consists of layers of surfactants (with or without cosurfactants) separated by solvent (oil or water). The H$_I$ consists of cylindrical surfactant micelles (with or without cosurfactant) with water in between. The H$_{II}$ consists of inverse surfactant monolayers (with or without cosurfactant) with oil in between. Block copolymers (e.g., diblock, or triblock) can be used instead of surfactants.

A second class of lyotropic L$^C$s that were created with the methods of the invention include "hybrid" L$^C$ phases comprising surfactants, e.g., lipids, (or block copolymers) complexed with macromolecules (e.g. polyelectrolytes such as DNA, RNA, polypeptides). Initial phase diagram containing such structures are shown in FIGS. 12 and 11b.

The L$_\alpha{}^C$, the H$_I{}^C$, and H$_{II}{}^C$ structures can contain an additional macromolecular component, e.g., a cosurfactant. The addition of the cosurfactant changes the mechanical properties of the lubricants at the molecular level; e.g. by changing the diameter and elastic (torsional, bending) moduli of the macromolecules.

These lubricants would be useful in methods to reduce friction between two surfaces. This method comprises contacting the surfaces with the lubricant of the invention so as to reduce friction between the two surfaces when the surfaces are put in contact.

The invention also provides methods for creating a pattern on a surface. In one embodiment, the method comprises applying the macromolecule-lipid complexes of the invention on the surface so as to create a pattern thereon. In accordance with the practice of the invention, the pattern is used to create a mask.

The present invention further provides methods for creating a material having desired properties. In one embodiment, the method comprises applying a macromolecule-lipid complex to a surface by the method of above. Additionally, the material can be applied to the complex so that the molecules of the material can self-assemble based on its interactions with the complex. The complex is then removed from the surface thereby creating the material having the regulated structure. In accordance with the practice of the invention, the complex can be in a multilamellar, regular hexagonal, or inverted hexagonal phase. Additionally, the material so created can be used as a molecular sieve for separating molecules based on size.

Compositions of the Invention

The present invention provides nucleic acid-lipid complexes comprising a charged lipid combination and a charged nucleic acid molecule. In one embodiment of the invention, the charge of the lipid combination is opposite of the charge of the nucleic acid molecule. Further, the resulting complex has a desired isoelectric point state and nucleic acids exhibiting interaxial spacing of greater than 24.5 angstroms. In another embodiment, the interaxial spacing range is about between 24.5 and 60 angstroms. In yet another embodiment, the interaxial spacing is about 60 angstroms. In accordance with the practice of the invention, the conformation of the resulting complex can be a multilamellar structure with alternating lipid bilayers and nucleic acid monolayers.

Suitable examples of nucleic acid molecules include, but are not limited to, deoxyribonucleic acid (DNA), ribonucleic acid (RNA). The macromolecules may be linear, circular, nicked circular or supercoiled. The nucleic acid molecules can have phosphate backbones but not necessarily so. Alternatively, nucleic acid molecules having non-phosphate backbones which improve binding are also encompassed within this invention.

In one embodiment, the complex comprises a charged lipid combination; and a charged nucleic acid molecule. The charge of the lipid combination can be opposite of the charge of the nucleic acid molecule. Further, the lipid and the nucleic acid molecule are associated so as to form a complex in an isoelectric point state. In this state, the relative amounts of the lipid components generates the lipid bilayer membrane having a thickness of between 25 and 75 angstroms. Additionally, the conformation of the complex has nucleic acids exhibiting interaxial spacing of a range between 50 and 75 angstroms.

The present invention further provides macromolecule-lipid complexes comprising a charged lipid combination; and a charged macromolecule. Examples of suitable macromolecules include, but are not limited to, nucleic acid molecules such as single or double stranded deoxyribonucleic acid (DNA) or ribonucleic acid (RNA) or hybrids thereof, or modified analogs thereof of varying lengths. In addition, the macromolecule can be a peptide, a protein (or modified analogs thereof). Further, the macromolecule may be a drug such as a chemotherapeutic agent or a modified analog thereof.

In one embodiment of the macromolecule-lipid complex the charge of the lipid combination is opposite of the charge of the nucleic acid molecule. Also, the lipid and the nucleic acid molecule are associated so as to form a complex in an isoelectric point state.

The lipid combination can have a charge lipid component and a neutral lipid component. The amount of the neutral lipid component relative to the charged lipid component can range from 2 to 95 percent.

Alternatively, in another embodiment of the macromolecule-lipid complex, the amount of the neutral lipid component relative to the charged lipid component ranges from 55 to 95 percent. Also, in accordance with the practice of the invention, the ratio of the neutral lipid component relative to the charged lipid component can be 70/30.

Suitable lipids include, but are not limited to, dioleoyl phophatidyl choline or dioleoyl phophatidyl ethanolamine and dioleoyl triethylammonium propane combination.

In a further embodiment of the macromolecule-lipid complex, the lipid combination can be a charged lipid combination and the macromolecule can be a charged macromolecule. The lipids form a bilayer membrane in the complex to which the charged macromolecule can be associated. In this embodiment, the charge of the lipid combination can be opposite of the charge of the nucleic acid molecule. Further, the lipid and the nucleic acid molecule are associated so as to form a complex in an isoelectric point state. Additionally, the relative amounts of the lipid components generates the lipid bilayer membrane having a thickness of between 25 and 75 angstroms.

In another embodiment of the macromolecule-lipid complex, the lipid and the nucleic acid molecule are associated so as to form a complex in a positively charged state, wherein the lipids form a bilayer membrane to which charged macromolecule is associated, and the relative amounts of the lipid components generates the lipid bilayer membrane having a thickness of between 41 and 75 angstroms.

Also, in another embodiment of the macromolecule-lipid complex, the lipid and the nucleic acid molecule are associated so as to form a complex in a negatively charged state, wherein the lipids form a bilayer membrane to which charged macromolecule is associated, and the relative amounts of the lipid components generates the lipid bilayer membrane having a thickness of between 32 and 75 angstroms.

In accordance with the practice of the invention, the lipid can be dioleoyl phophatidyl cholin or dioleoyl phophatidyl ethanolamine and dioleoyl triethylammonium propane. In this embodiment, the charge of the lipid combination in the complex can be opposite of the charge of the nucleic acid molecule. The dioleoyl phophatidyl cholin or dioleoyl phophatidyl ethanolamine and dioleoyl triethylammonium propane form a bilayer membrane to which the charged macromolecule is associated in an isoelectric point state, wherein the relative amounts of dioleoyl phophatidyl cholin or dioleoyl phophatidyl ethanolamine lipids relative to the dioleoyl triethylammonium propane generates the lipid bilayer membrane having a thickness of between 25 and 75 angstroms.

In accordance with the practice of this invention, in the macromolecule-lipid complex, the amount of the neutral lipid component relative to the charged lipid component ranges from 0 to 95 percent and whose charge is approximately zero. Alternatively, the amount of the neutral lipid component relative to the charged lipid component ranges from 55 to 95 percent and which has either a positive or negative charge.

There is a great flexibility in the structure of these complexes, which may vary greatly in their molecular ordering. These complexes may be relatively simple or may consist of a highly ordered structure. For example the conformation of such a complex can include a multilamellar structure with alternating lipid bilayers and nucleic acid monolayers.

The invention further provides formulations which form the basis for the processing of templates and for producing molecular sieves with precise control over pore size.

The invention provides a macromolecule-lipid complex having as components of the complex (1) a macromolecule or macromolecules, (2) a lipid or lipid combination, and (3) a cosurfactant or cosurfactants. The addition of the cosurfactant reduces the elastic cost and decrease the membrane rigidity thus allowing a more favorable environment for the transition from lamellar phase to hexagonal or inverted hexagonal phase. In accordance with the practice of the invention, the lipid can be substituted by any surfactant. Although, lipids are preferred.

Also in accordance with the practice of the invention, the macromolecule and lipid can be charged. For example, when the macromolecule is charged, the lipid can be neutral. Preferably, the charge of the macromolecule is opposite to the charge of the lipid.

Suitable examples of cosurfactant molecules include but is not limited to an alcohol. The alcohol can be butanol, pentanol, hexanol, heptanol, octanol, nonanol, and geraniol. Other biologically derived alcohols is acceptable.

The lipids can be cationic, anionic or neutral. Examples of suitable cationic lipids include but are not limited to DOTMA, DDAB, CTAB, and DOTAP. A suitable lipid is a phospholipid, e.g, lecithin, phophatidylinositol, sphingomyelin, cardiolipin, phosphatidic acid and the cerebrosides. Other lipids include stearylamine, dicetyl phosphate, cholesterol and tocopherol.

Examples of suitable noncationic lipids include phosphatidyl choline, cholesterol, phosphatidylehtanolamine, dioleoylphosphatidyl choline, dioleoylphophatidyl glycerol., and dioloeoylphosphatidyl ethanolamine.

Examples of suitable macromolecule include nucleic acid molecules (DNA, RNA, hybrids thereof, or nucleoside), proteins, peptides, immunomodulating compounds, glycoproteins, lipoproteins, hormones, neurotransmitters, tumoricidal agents, growth factors, toxins, analgesics, anesthetics, monosaccharides, polysaccharides, narcotics, catalysts, enzymes, antimicrobial agents, anti-inflammatory agents, anti-parasitic agents, dyes, radiolabels, radio-opaque compounds, and fluorescent compounds.

The following examples are presented to illustrate the present invention and to assist one of ordinary skill in making and using the same. These examples are not intended in any way to otherwise limit the scope of the invention.

EXAMPLE 1

Cationic liposomes complexed with DNA (CL-DNA) are promising synthetically based nonviral carriers of DNA vectors for gene therapy. The solution structure of CL-DNA complexes was probed on length scales from subnanometer to micrometer by synchrotron x-ray diffraction and optical microscopy. The addition of either linear $\lambda$-phage or plasmid DNA to CLs resulted in an unexpected topological transition from liposomes to optically birefringent liquid crystalline condensed globules. X-ray diffraction of the globules reveals a novel multilamellar structure with alternating lipid bilayer and DNA monolayers. We discovered that $\lambda$-DNA chains form a one-dimensional lattice with distinct interhelical packing states. Remarkably, in the isoelectric point state, the $\lambda$-DNA interaxial spacing expands between 24.5 and 60 angstroms upon lipid dilution and is indicative of a long-range electrostatic-induced repulsion possibly enhanced by chain undulations.

We have carried out a combined in situ optical microscopy and x-ray diffraction (XRD) study of CL-DNA complexes (an embodiment of a macromolecule-lipid complex). On semi-macroscopic length scales, the addition of linear or circular plasmid DNA to binary mixtures of cationic liposomes induces a topological transition from liposomes into collapsed condensates in the form of optically birefringent LC globules with size on the order of 1 $\mu$m.

The solution structure of the globules was revealed on the 1 to 100 nm length scale by high-resolution synchrotron XRD studies. Unexpectedly, the complexes consist of a higher ordered multilamellar structure with DNA sandwiched between cationic bilayers.

We have discovered distinct interhelical packing states for linear $\lambda$-phage DNA, above and below, and at the isoelectric point of the complex by varying the concentrations of DNA and the lipid components comprising the complex. Remarkably, in the isoelectric state of the CL-DNA complex the DNA interaxial distance $d_{DNA}$ increases from 24.5 to 60 Å as a function of lipid dilution and is quantitatively consistent with an expanding one-dimensional (1D) lattice of DNA chains. Thus, the DNA chains confined between bilayers form a novel 2D smectic phase.

DNA molecules can be readily labeled and imaged by fluorescence microscopy (16). Free λ-DNA in aqueous solution appears as a highly dynamic blob of ≈1 μm in diameter, in agreement with a classical random coil configuration, while the contour length of λ-phage DNA is 16.5 μm. The CLs consisted of binary mixtures of lipids which contained either DOPC (dioleoyl phosphatidyl cholin) or DOPE (dioleoyl phosphatidyl ethanolamine) as the neutral co-lipid and DOTAP (dioleoyl trimethylammonium propane) as the cationic lipid. A mixture of DOPE/DOTAP (1:1, wt:wt) was prepared in a 20 mg/ml chloroform stock solution. 500 ml was dried under nitrogen in a narrow glass beaker and desiccated under vacuum for 6 hours. After addition of 2.5 ml Millipore water and 2 hr incubation at 40° C. the vesicle suspension was sonicated by clarity for 10 minutes. The resulting solution of liposomes, 25 mg/ml was filtered through 0.2 μm Nucleopore filters. For optical measurements the concentration of SUV used was between 0.1 mg/ml and 0.5 mg/ml. All lipids were purchased from Avanti Polar Lipids, Inc. (Alabaster, Alabama).

The DOTAP/DOPC and DOTAP/DOPE CLs had a size distribution ranging between 0.02 to 0.1 μm in diameter, with a peak around 0.07 μm (the liposome and complex sizes were measured by dynamic light scattering (Microtrac UPA 150, Leeds and Northrup). We used highly purified linear λ-phage DNA (48,502 bp) in most of the experiments but some were carried out with *Escherichia coli* DNA and pBR322 plasmid DNA (4361 bp); the latter, consisted of a mixture of nicked circular and supercoiled DNA. Purified λ-phage DNA and pBR322 plasmid were purchased from Biolabs, New England. Optical and x-ray data were taken with linear λ prepared in 2 ways: (1) used as delivered, and (2) by heating to 65° C. and reacting with a surplus of a 12-base oligo complementary to the 3' COS end. Subsequently the DNA was ligated (T4 DNA ligase, Fischer). The methods gave the same result. For the optical experiments the DNA concentration used was between 0.01 mg/ml and 0.1 mg/ml. Condensation of CLs with λ-DNA was directly observed using differential interference microscopy (DIC) and fluorescence microscopy. A Nikon Diaphot 300 equipped for epifluorescence and high resolution DIC was used.

Figure 1A:
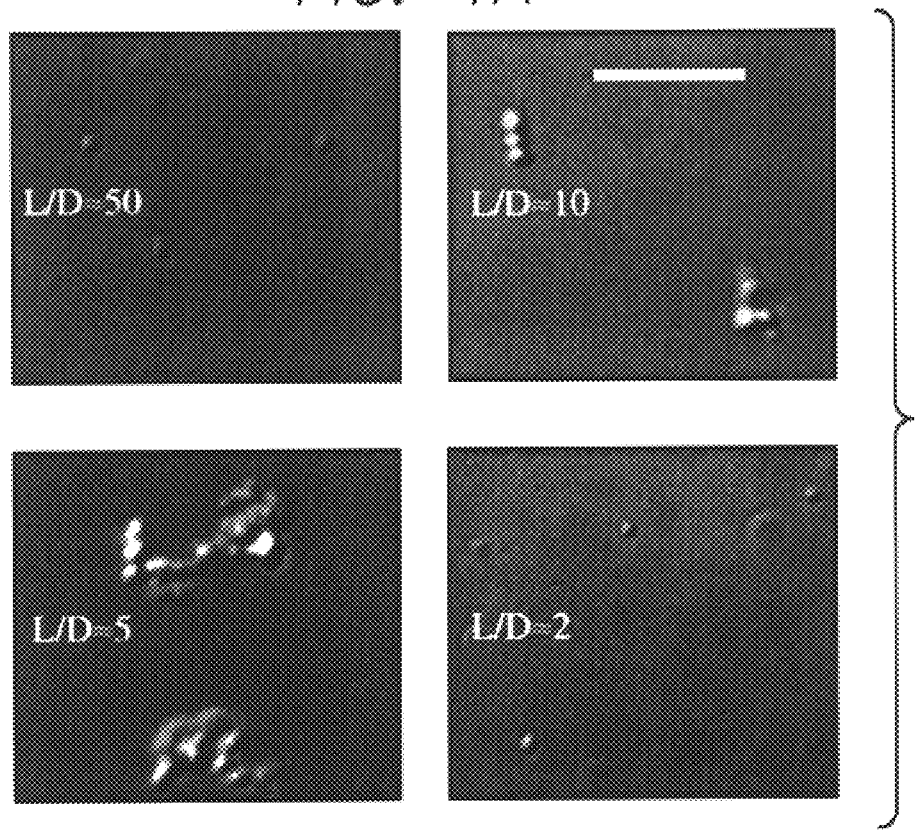
FIG. 1(A) is a series of high resolution differential interference contrast microscopy images of cationic liposome-DNA complexes showing the formation of distinct condensed globules in mixtures of different lipid to DNA weight ratios. The scale bar is 10 μm.

We show in FIG. 1A a series of DIC images 30 min after preparation in CL-DNA mixtures as a function of the total lipid to λ-DNA weight ratio L/D, where L=DOTAP+DOPE denotes the weight of lipid and D the weight of DNA. FIG. 1A shows high-resolution DIC images of CL-DNA complexes forming distinct condensed globules in mixtures of different lipid to DNA weight ratio (L/D); scale bar is 10 μm.

Similar images were observed with λ-DNA replaced by the pBR322 plasmid DNA or DOPE replaced by DOPC. At low DNA concentrations (FIG. 1A, L/D=50), in contrast to the pure liposome solution where no objects >0.2 μm were found, 1 μm large globules are observed. The globules coexist with excess liposomes. As more DNA is added, the globular condensates form larger chain like structures (FIG. 1A, L/D=10). The Brownian motion of these globules suggests that they are linked by an invisible thread. At L/D=5 the chain-like structures flocculate into large aggregates of distinct globules. For L/D<5, the complex size was smaller and stable in time again (FIG. 1A, L/D=2), and coexisted with excess DNA. Fluorescence-labeled DNA and lipid can be detected on each globule, indicating that the globules are DNA-lipid condensates. Sonicated DOPE-DOTAP (1:1) liposomes were prepared at 0.1 mg/ml with 0.2 mol % DHPE-Texas Red fluorescence label. DNA stained by YOYO (Molecular Probes) was added under gentle mixing at different lipid-to-DNA ratios (L/D). Polarized microscopy also shows that the distinct globules are birefringent indicative of their LC nature.

Figure 1B:
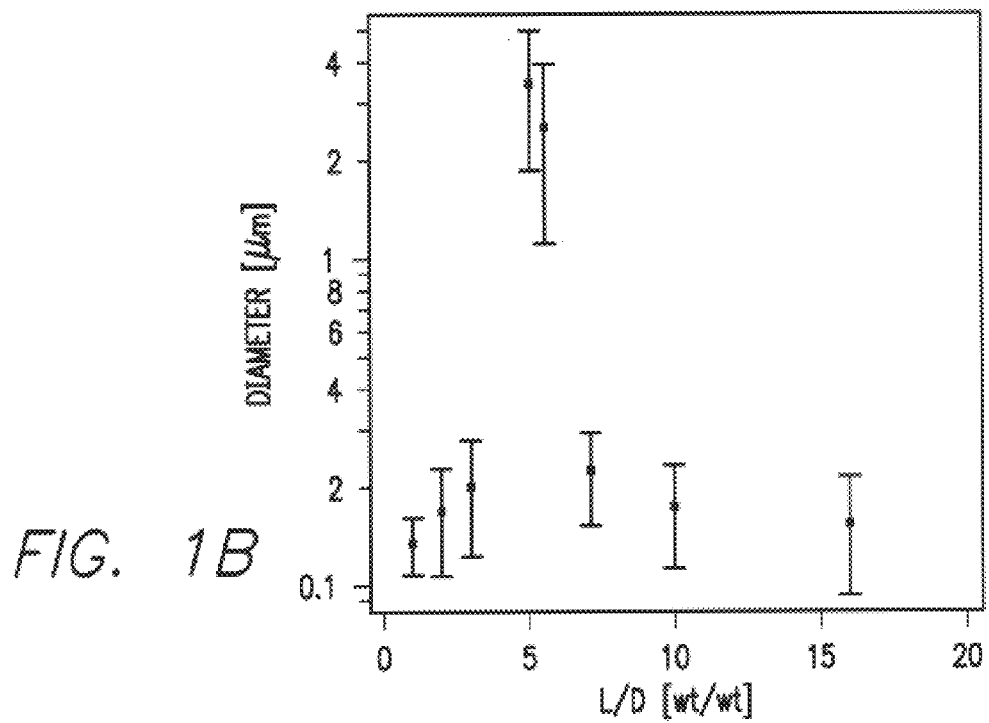
FIG. 1(B) is a plot of the average size of the lipid-DNA complexes measured by dynamic light scattering.

The size dependence of the complexes as a function of L/D (FIG. 1B) was independently measured by dynamic light scattering (the liposome and complex sizes were measured by dynamic light scattering (Microtrac UPA 150, Leeds and Northrup). The large error bars represent the broad polydispersity of the system. The size dependence of the aggregates can be understood in terms of a charge-stabilized colloidal suspension. The charge of the complexes was measured by their electrophoretic mobility in an external electric field. For L/D>5 (FIG. 1A; L/D=50 or 10) the complexes are positively charged, while for L/D<5 (FIG. 1A; L/D=2) the complexes are negatively charged. The charge reversal is in good agreement with the stoichiometrically expected charge balance of the components DOTAP and DNA at L/D=4.4 where L=DOTAP+DOPE in equal weights. Thus, the positively and negatively charged globules at L/D=50 and L/D=2 respectively, repel each other and remain separate, while as L/D approaches 5, the nearly neutral complexes collide and tend to stick due to van der Waals attraction. Remarkably, the size of the globules appears to be only weakly dependent on the length of the DNA in similar experiments carried out with *Escherichia coli* DNA or pBR322 plasmid (4361 bp).

Figure 2A:
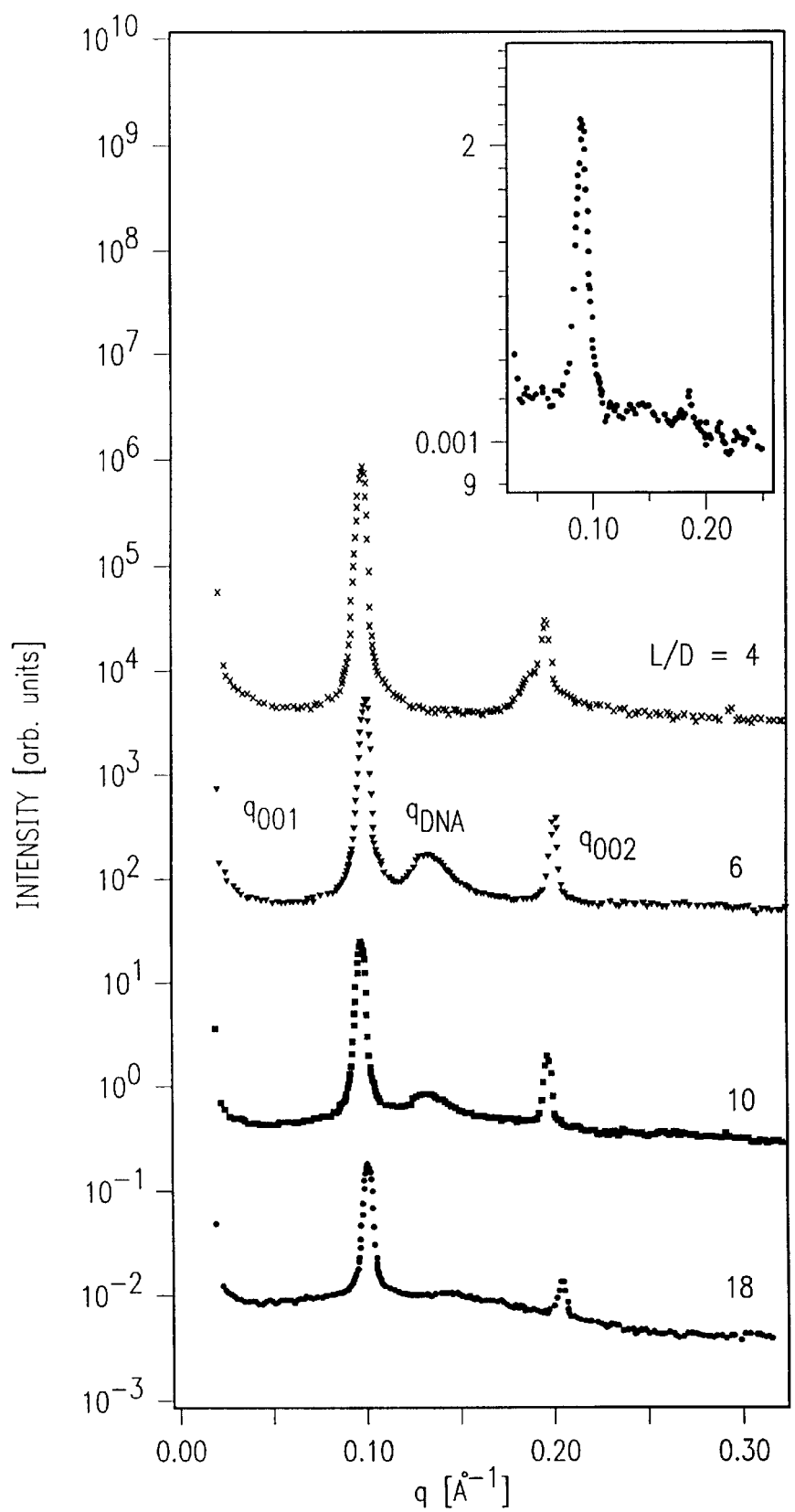
FIG. 2(A) is a series of small-angle x-ray scattering scans in water as a function of different lipid to DNA weight ratio (L/D). (Inset is under extreme dilute conditions).

FIG. 2A shows a series of SAXS scans of CL-DNA complexes in excess water as a function of different lipid to DNA weight ration (L/D). The Bragg reflections at $q_{011}$=0.096 Å$^{-1}$ and $q_{002}$=0.1.92 Å$^{-1}$ result from the multilamellar $L_\alpha$ structure with intercalated monolayer DNA (see FIG. 3A). The intermediate peak at $q_{DNA}$ is due to the DNA-interaxial spacing $d_{DNA}$ as described in the text. Inset: SAXS scan of an extremely dilute (lipid+DNA=0.014% volume in water) λ-DNA-DOPE/DOTAP (1:1) complex at L/D=10, which shows the same features as the more concentrated mixtures and confirms the multilamellar structure (with alternating lipid bilayer and DNA monolayers) of very dilute mixtures typically used in gene therapy applications.

Figure 2B:
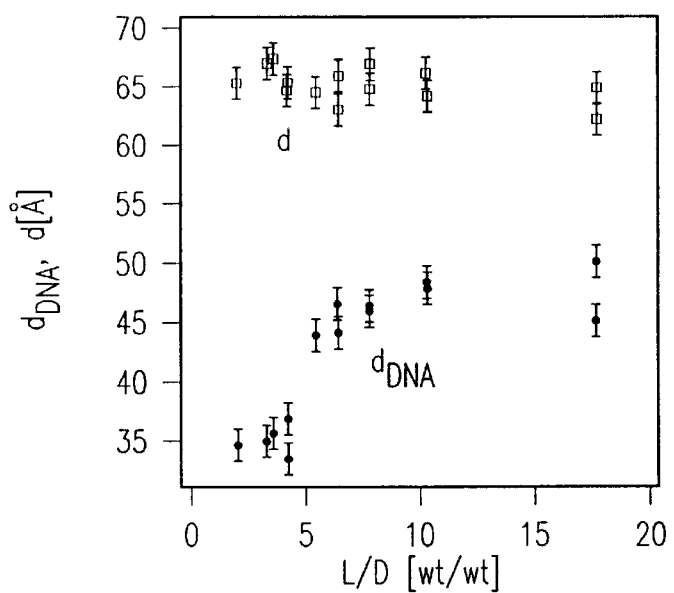
FIG. 2(B) is plot of the spacing d and $d_{DNA}$ as a function of L/D.
Figure 2C:
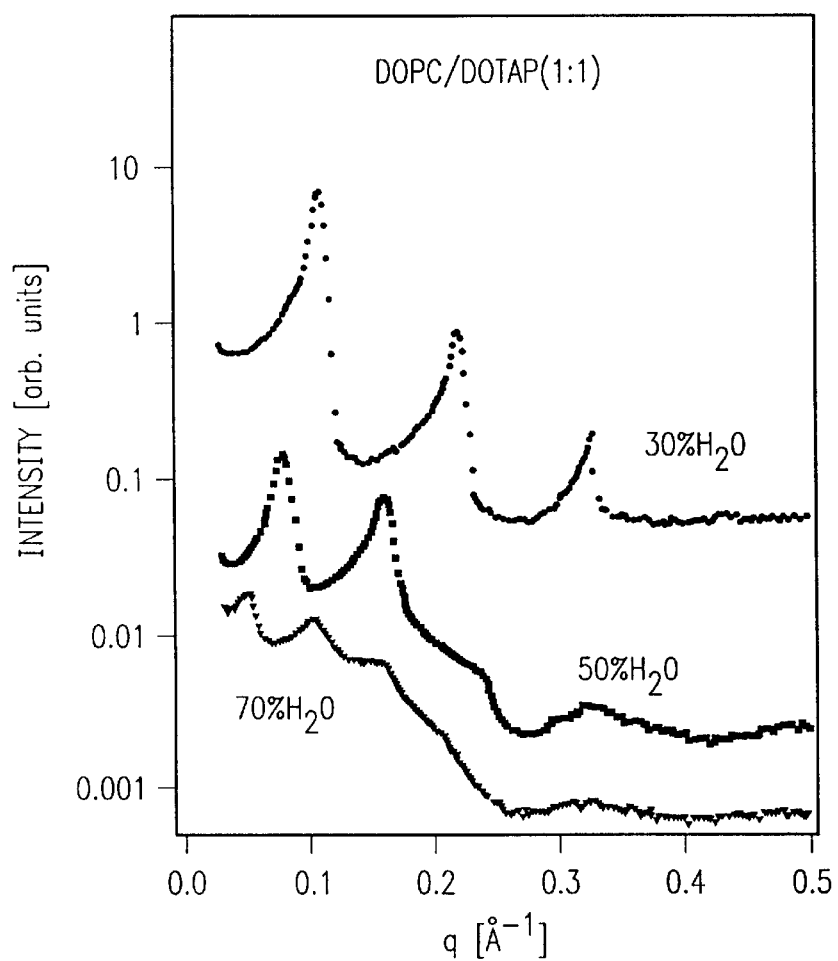
FIG. 2(C) is a series of small-angle x-ray scattering scans of the lamellar Lα phase of DOPC/DOTAP water mixtures done at lower resolution (rotating anode x-ray generator).

The XRD experiments revealed unexpected structures for mixtures of CLs and DNA. FIG. 2B shows the spacings d and $d_{DNA}$ as a function of L/D show that (i) d is nearly constant and (ii) two distinct states of DNA packing, one where the complexes are positive (L/D>5, $d_{DNA}$ approximately 46 Å) and the other state where the complexes are negative (L/D>5, $d_{DNA}$ approximately 35 Å) FIG. 2C shows SAXS scans of the lamellar Lα phase of DOPC/DOTAP (cationic)-water mixtures done at lower resolution (rotating-anode x-ray generator). A dilution series of 30% (d=57.61 Å), 50% (d=79.49 Å), and 70% (d=123.13 Å) H$_2$O by weight is shown. High resolution synchrotron x-ray scattering were performed at the Stanford Synchrotron Radiation Laboratory. Lower resolution XRD experiments were performed using a rotating anode source.

Small angle x-ray scattering (SAXS) data of dilute ($\Phi_w$= the volume fraction of water=98.6%±0.3%) DOPC/DOTAP (1:1)-λ-DNA mixtures as a function of L/D (L=DOPC+DOTAP) (FIG. 2A) are consistent with a complete topological rearrangement of liposomes and DNA into a multilayer structure with DNA intercalated between the bilayers (23)

(FIG. 3A). The DNA-lipid condensates were prepared from a 25 mg/ml liposome suspension and a 5 mg/ml DNA solution. The solutions were filled in 2 mm diameter quartz capillaries with different ratios L/D respectively and mixed after flame sealing by gentle centrifugation up and down the capillary.

FIG. 3A shows a schematic picture of the local arrangement in the interior of lipid-DNA complexes (shown at two different concentrations in FIG. 1A and in FIG. 3B below. The semiflexible DNA molecules are represented by rods on this molecular scale. The neutral and cationic lipids comprising the membrane are expected to locally demix with the cationic lipids (red) more concentrated near the DNA. Micrographs of DNA-lipid condensates under (B) bright light and (C) crossed polarizers showing LC-like defects. Two sharp peaks at q=0.0965±0.003 and 0.193±0.006 Å$^{-1}$ correspond to the (001) peaks of a layered structure with an interlayer spacing d(=$\delta_m$+$\delta_w$) which is in the range 65.1±2 Å(FIG. 2B, open squares). The membrane thickness and water gap are denoted by $\delta_m$ and $\delta_w$, respectively (FIG. 3A). The middle broad peak $q_{DNA}$ arises from DNA-DNA correlations and gives $d_{DNA}$ =2π/$q_{DNA}$ (FIG. 2B, solid circles). The multilamellar structure with intercalated DNA is also observed in CL-DNA complexes containing supercoiled DNA both in water, and also in Dulbecco's Modified Eagle Medium used in transfection experiments in gene therapy applications. This novel multilamellar structure of the CL-DNA complexes are observed to protect DNA from being cut by restriction enzymes. The intercalation of λ-DNA between membranes in CL-DNA complexes was found to protect it against a HindIII restriction enzyme which cuts naked λ-DNA at 7 sites (21).

In the absence of DNA, membranes comprised of mixtures of DOPC and the cationic lipid DOTAP (1:1) exhibit strong long-range interlayer electrostatic repulsions that overwhelm the van der Waals attraction (26, 27). In this case, as the volume fraction $\Phi_w$ of water is increased, the Lα phase swells and d is given by the simple geometric relation d=$\delta_m$/(1−$\Phi_w$) (26). The SAXS scans in FIG. 2C shows this behavior with the (001) peaks moving to lower q as $\Phi_w$ increases. From d(=2 π/$q_{(001)}$) at a given $\Phi_w$ we obtain $\delta_m$=39±0.5 Å for DOPC/DOTAP (1:1). Liposomes made of DOPC/DOTAP (1:1) with $\Phi_w$=98.5% do not exhibit Bragg diffraction in the small wave-vector range covered in FIG. 2A.

The DNA that condenses on the CLs strongly screens the electrostatic interaction between lipid bilayers and leads to condensed multilayers. The average thickness of the water gap $\delta_w$=d−$\delta_m$=65.1 Å−39 Å=26.1 Å±2.5 Å is, just sufficient to accommodate one monolayer of B-DNA (diameter=20 Å) including a hydration shell (28). We see in FIG. 2B that d is almost constant as expected, for a monolayer DNA intercalate (FIG. 3A). In contrast, as L/D decreases from 18 to 2, $d_{DNA}$ suddenly decreased from=44 Å in the positively charged state just above L/D=5 (near the stoichiometric charge neutral point) to=37 Å for the negatively charged state (FIG. 2B). In these distinct states, lamellar condensates coexist with excess giant liposomes in the positive state, and with excess DNA in the negative state. The multilamellar structure of the complex (with λ-DNA) and the distinct DNA interhelical packing states was also found in SAXS data in binary mixtures of cationic lipids which contained DOPE [which has a high transfection efficiency (2)] as the neutral co-lipid. However, the complexes showed a phase-separation into two lamellar phases.

The driving force for higher order self-assembly is the release of counterions. DNA carries 20 phosphate groups per helical pitch of 34.1 Å, and due to Manning condensation 76% of these anionic groups are permanently neutralized by their counterions, which leads to a distance between anionic groups=the Bjerrum length=7.1 Å (30). During condensation, the cationic lipid tends to fully neutralize the phosphate groups on the DNA in effect replacing and releasing the originally condensed counterions (both those bound to the ID DNA and to the 2D cationic membranes) in solution.

To improve on the signal-to-background intensity ratio the synchrotron XRD experiments were carried out at concentrations (lipid+DNA=1.4±0.3% volume in water), which, although dilute, were nevertheless greater than the concentrations used in the microscopy work. The DNA-lipid condensates were prepared from a 25 mg/ml liposome suspension and a 5 mg/ml DNA solution. The solutions were filled in 2 mm diameter quartz capillaries with different ratios L/D respectively and mixed after flame sealing by gentle centrifugation up and down the capillary.

A typical SAXS scan in mixtures at the optical microscopy concentrations (FIG. 1A) is shown in FIG. 2A (inset) which exhibits the same features and confirms that the local multilayer and DNA structure (FIG. 3A) is unchanged between the two concentrations. The x-ray samples consisted of connected yet distinct globules (FIG. 3B). What is remarkable is the retention of the globule morphology consistent with what was observed at lower concentrations in DIC (FIG. 1A). Under crossed polarizers (FIG. 3C) LC defects, both focal conics and spherulites (31), resulting from the smectic-A-like layered structure of the DNA-lipid globules are evident. The globules at the lower concentrations (FIG. 1A) show similar LC defects.

We further probed the nature of λ-DNA-packing within the lipid layers by conducting a lipid dilution experiment in the isoelectric point state of the complex. The total lipid (L=DOTAP+DOPC) was increased while the charge of the overall complex, given by the ratio of cationic DOTAP to DNA, was kept constant at DOTAP/DNA=2.40±0.1. The projected charge density of DNA (two anionic charges per 68 Å$^2$) is very nearly matched by two cationic head groups on DOTAP of=70 Å$^2$ each and thus permits near complete neutralization of the complex (FIG. 3A).

Figure 4A:
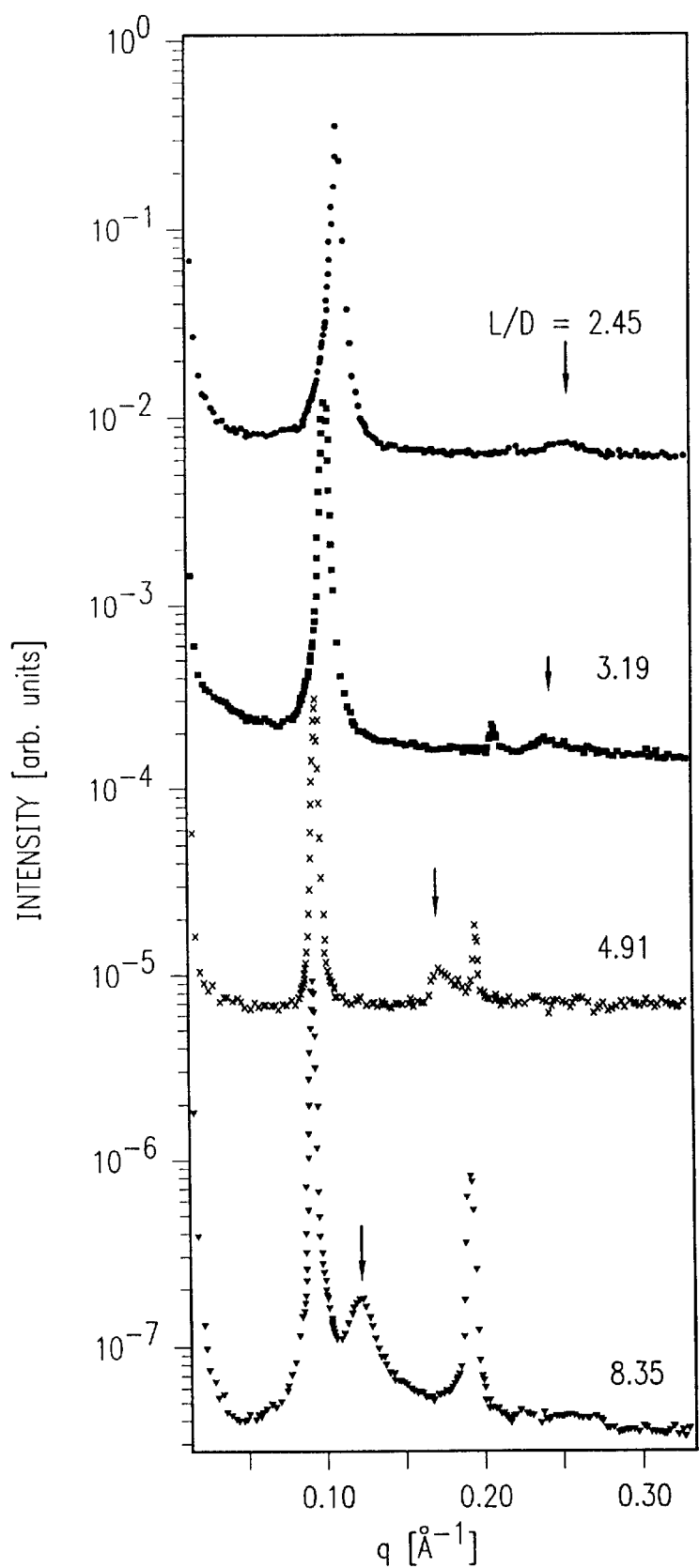
FIG. 4(A) is a series of small-angle x-ray scattering scans of CL-DNA complexes at approximately the isoelectric point.
Figure 4B:
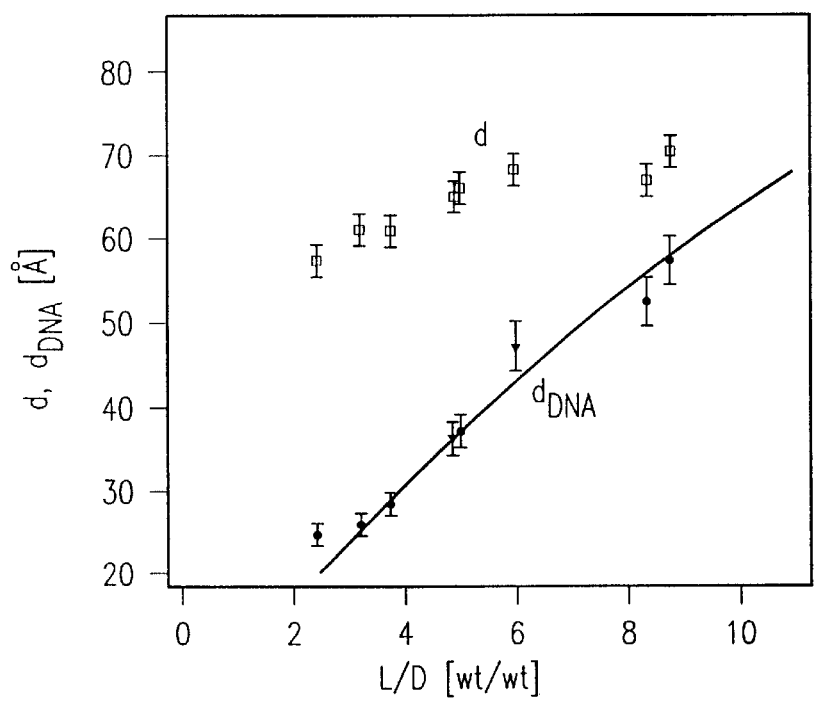
FIG. 4(B) is $d_{DNA}$ and d from FIG. 4(A) plotted as a function of L/D.
Figure 4C:
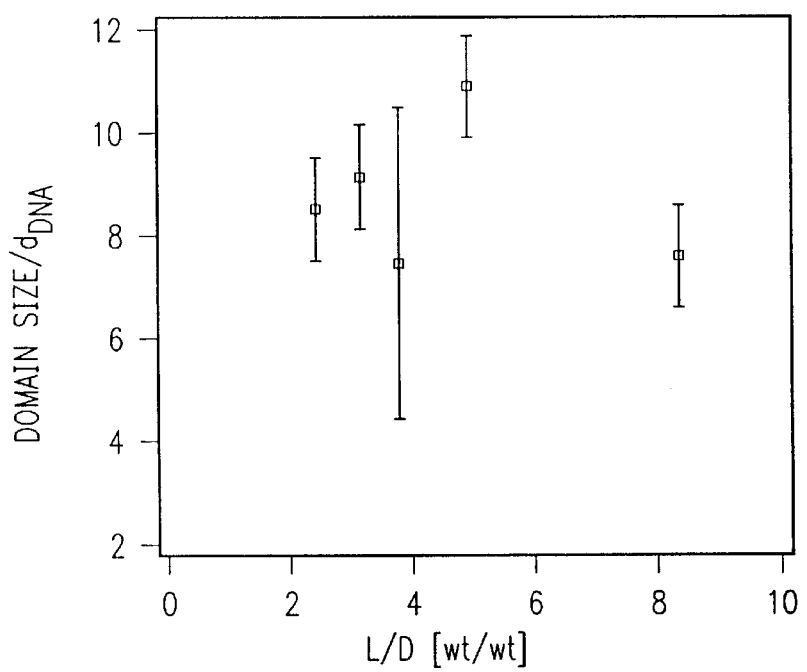
FIG. 4(C) the average domain size of the 1D lattice of DNA chains derived from the width of the DNA peaks shown in 4(B).

FIG. 4A shows a series of SAXS scans of CL-DNA complexes at DOTAP/DNA=2.4±0.1 (approximately the isoelectric point) which shows the DNA peak (arrow) moving toward smaller q as L/D increases (that is, increasing the DOPC to DOTAP ratio at a constant DOTAP/DNA; L=DOTAP+DOPC,D=DNA). FIG. 4B shows $d_{DNA}$ and d from (A) plotted as a function of L/D (see FIG. 2A for notation). Circles are synchrotron data, and triangles are rotating anode. The solid line is the prediction of a packing calculation (with no adjustable parameters) where the DNA chains form a space-filling 1D lattice. FIG. 4C shows the average domain size of the 1D lattice of DNA chains derived from the width of the DNA peaks shown in (B) [corrected for resolution and powder averaging broadening effects]. The SAXS scans in FIG. 4A, (arrow points to the DNA peak) show that $d_{DNA}$=2π/$q_{DNA}$ increased, with lipid dilution from 24.54 Å to 73.5 Å as L/D increased with lipid dilution between 2.45 and 13.8 (FIG. 4B). The most compressed interaxial spacing of 24.55 Å at L/D=2.45 approaches the short-range repulsive hard-core interaction of the B-DNA rods containing a hydration layer (28).

The DNA interaxial spacing can be calculated rigorously from simple geometric considerations. If we assume that all of the DNA is adsorbed between the bilayers and that the orientationally ordered DNA chains separate to fill the increasing lipid area as L/D increases, while maintaining a 1D lattice (FIG. 3A), then:

$$d_{DNA} = \frac{A d\rho_D}{\delta_m \rho_L} \cdot (L/D) \qquad (1)$$

Here, $\rho_D=1.7$ (g/cc) and $\rho_L=1.07$ (g/cc) denote the densities of DNA and lipid respectively, $\delta_m$ the membrane thickness, and $A_D$ the DNA area. $A_D=Wt(\lambda)/(\rho_D L(\lambda))=186$ Å$^2$, Wt($\lambda$)=weight of $\lambda$-DNA=$31.5\times10^6/(6.022\times10^{23})$ g and L($\lambda$)=contour length of $\lambda$-DNA=$48502\times3.4$ Å. The solid line in FIG. 4B is then obtained from Eq. 1 with no adjustable parameters and clearly shows a remarkable agreement with the data over the measured interaxial distance from 24.5 to 73.5 Å. The observed deviation from linear behavior both in the data and the solid line arises from the slight increase in $\delta_m$ as L/D increases. The variation in the interlayer spacing $d(=\delta_w+\delta_m)$ (FIG. 4B) arises from the increase in the membrane bilayer thickness $\delta_m$ as L/D increases (each DOPC molecule is=4 Å to 6 Å longer than a DOTAP molecule). $\delta_m$ was obtained at each L/D by measuring d in the L$\alpha$ phase multilayer membranes at the corresponding DOTAP to DOPC ration and using the relation $\delta_m = d(1-\Phi_w)$, $\Phi_w$=water volume fraction. The measured $\delta_m$ and d, gave $\delta_w=25$ Å$\pm1.5$ Å close to the spacing for the DNA monolayer (see FIG. 3A).

The existence of a finite-sized ordered lattice is made unambiguous from the line widths of the DNA peaks (FIG. 4A) where we find that the 1D lattice of DNA chains has a correlated domain size extending to near 10 unit cells (FIG. 4C). Thus, the DNA chains form a 1D ordered array adsorbed between 2D membranes; that is, they form a novel finite-sized 2D smectic phase.

The lattice expansion at the isoelectric point covering interaxial distances with negligible short-range hydration forces (28) (B-DNA diameter≈20 Å) is indicative of a long-range repulsion. The distribution of the counterion lipid (DOTAP) concentration according to the Poisson-Boltzmarm equation along the top and bottom monolayer which bound the DNA molecules (FIG. 3A) will lead to a long-range electrostatic-induced interhelical interaction from the counterion lipid pressure (due to the expected local demixing of the cationic and neutral lipids) and the electric field. Preliminary salt dependent experiments which show shifts in the DNA peak indicate that long-range electrostatic induced interactions are present. Additionally, because of the semi-flexible nature of $\lambda$-DNA [consisting of between 170 and 340 persistence lengths ($\xi_p$) in dilute solution ($\xi_p\approx$between 500 and 1000 Å)], we expect the long-range repulsions to be further enhanced by chain-undulation interactions. A similar enhancement has been observed in a hexagonal lattice of DNA (28, 34). This phase of 1D DNA chains is the lower dimensional analog of 2D fluid membranes in that it may either be dominated by electrostatic-induced forces (26, 27) or the interplay between electrostatics and undulations (35–37).

Further experiments are needed to elucidate the precise nature of the intermolecular forces and the interplay between electrostatic and chain undulation interactions (38). Future studies may also reveal states with 3D correlations between the DNA chains from layer to layer in analogy to recent theoretical findings in highly condensed DNA phases (39). The observed quantitative control over the structural nature of the DNA packing in CL-DNA complexes may lead to a better understanding of the important structural parameters relevant to transfection efficiencies in gene therapy; in particular, they should be directly relevant to our understanding of the interactions of the complex with cellular lipids and the mechanism of DNA transfer across the nuclear membrane.

EXAMPLE 2

This example provides the hexagonal phase of a cationic lipid-polyelectrolyte complex (an embodiment of a macromolecule-lipid complex). This embodiment is a LC structure of the complex achieved by varying the lipid composition. It is a novel LC phase with DNA double-strands surrounded by lipid monolayers arranged on a regular hexagonal lattice. This embodiment interacts differently with giant negatively charged liposomes, compared to the lamellar phase, and represents the simplest model of outer cellular membranes. We demonstrate the generality of the lamellar-hexagonal transformation by observing it in complexes of cationic lipid with two other negatively charged biopolymers-polyglutamic acid (PGA), a model polypeptide and poly-thymine (polyT), a model single-stranded oligonucleotide. We identify the interactions leading to the transformations between the two complex phases for the three different biological polyelectrolytes. Aside from the significance for gene therapy, our findings suggest new pathways for controlling structural parameters of polyelectrolyte-surfactant complexes, which has been suggested as templates for the formation of new soft materials.

Example 1 shows that mixing linear DNA with liposomes of DOPC/DOTAP mixtures leads to a topological transition into CL-DNA complexes of lamellar structure $L_\alpha^C$, where DNA monolayers are sandwiched between lipid bilayers (41). In this example, the existence of a completely different inverted hexagonal $H_{II}^C$ liquid-crystalline state in complexes of linear 1-DNA with liposomes of DOPE/DOTAP mixtures is unambiguously demonstrated for the first time using synchrotron small-angle x-ray diffraction and optical microscopy. We show how changing the ratio of cationic DOTAP to neutral DOPE lipid in the liposomes leads to CL-DNA complexes with lamellar or hexagonal structure (FIG. 5a).

The use of cationic lipids can be extended to deliver other negatively charged biopolymers into cells, in particular polypetide-based drugs and single-stranded oligonucleotides for antisense therapy (22, 23). We show that these polyelectrolytes also form complexes with cationic lipids of lamellar and hexagonal structure, similar to the CL-DNA complexes. Comparison of the three types of complexes allows to gain an insight on how the polyelectrolyte charge density and diameter tune the interactions between lipids and polymer, shifting the phase boundaries between $L_\alpha^C$ and $H_{II}^C$ complexes.

Figure 5A:
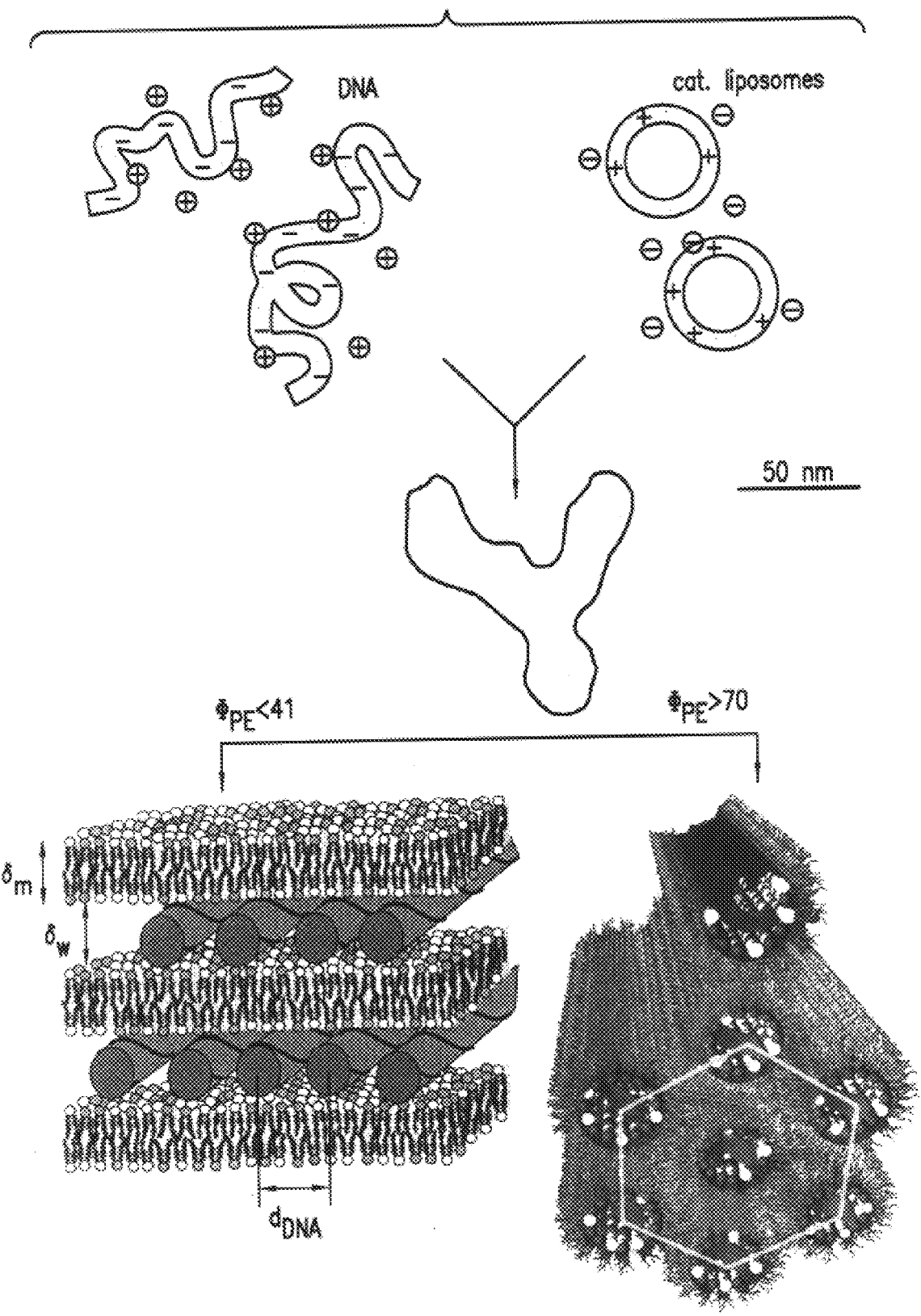
FIG. 5(A) is a schematic representation showing the macromolecule-lipid complex formation from the negatively charged DNA and positively charged liposomes. Schematics of lamellar $L_\alpha^C$ and inverted hexagonal complex $H_{II}^C$.

FIG. 5A shows the formation pathway of a complex from the free DNA and liposomes. 1-DNA in solution has a random-coil configuration of ~1 $\mu$m diameter. The Cls consisting of binary DOPE/DOTAP mixture have an average size of 0.06 $\mu$m. In order to reduce the electrostatic free energy, both DNA and lipid charges are partially neutralized by their respective counterions. During the CL-DNA complex formation cationic lipids replace DNA counterions, releasing the [Na$^+$] and [Cl$^-$] ions into solution with a very large entropic free energy gain (of order $k_B T$ per released counterion). The result is a close association between DNA and lipid in a compact complex of ~0.2 $\mu$m size. The overall charge of the complex is determined by the weight ratio r of cationic lipid and DNA. The complexes are positive for r>2.2 and negative for r<2.2, indicating that charge reversal occurs when complexes are stoichiometrically neutral with one positive lipid per each negatively charged nucleotide base.

Surprisingly, the internal structure of the complex changes completely with DOPE/DOTAP ratio. Defining the volume fraction of DOPE as $\Phi_{PE}$ as the fraction of neutral DOPE in the lipid mixture, the complex is lamellar $L_\alpha^C$ for $\Phi_{PE}<0.41$ and has inverted hexagonal $H_{II}^C$ structure for $\Phi_{PE}>0.7$. In complexes with $0.41<\Phi_{PE}<0.7$ the two structures coexist. Small-angle x-ray scattering (SAXS) data of complexes with $\Phi_{PE}=0.41$ and 0.75 (FIG. 5b) clearly shows the presence of two completely different structures. The two sharp peaks at q=0.099 Å$^{-1}$ and 0.198 Å$^{-1}$ correspond to (001) and (002) peaks of a lamellar structure with interlayer spacing d=63.4 Å. Since DOPE/DOTAP bilayer has thickness $\delta_m$=40 Å at $\Phi_{PE}$=0.41[13], the water gap between bilayers $d_w$=d−$d_m$=23.4 Å is just large enough to accommodate a monolayer of DNA with a hydration shell of water. This structure is analogous to the one previously reported in DOPC/DOTAP-DNA complexes (Example 1). The middle broad peak at $q_{DNA}$ arises from regular 2D-smectic arrangement of DNA, giving the spacing between the DNA strands $d_{DNA}=2^{II}/q_{DNA}$.

For $\Phi_{PE}>0.7$ the peaks of the SAXS scan index perfectly on a hexagonal lattice with a repeat spacing of a=4π/√3$q_{10}$=67.8 Å. We were able to observe Bragg peaks up to 7th order, indicating a high degree of regularity of the structure. Schematic of the new $H_{II}^C$ phase is shown in FIG. 5a. Each of the DNA molecules is surrounded by a monolayer of lipid and the unit cells of DNA/lipid inverted cylindrical micelles are arranged in a hexagonal lattice. The structure resembles that of the inverted hexagonal ($H_{II}$) phase of pure DOPE in excess water (30), with the water space inside the lipid micelle filled by DNA. The higher electron density of DNA with respect to water leads to the relative suppression of (22) and Bragg peak intensities compared with that in pure lipid $H_{II}$ phase. Assuming again an average bilayer thickness of 40 Å, the diameter of micellar void in the $H_{II}^C$ phase is ~28 Å, again sufficient for a DNA molecule with approximately two hydration shells.

To improve the signal/background ratio, samples for synchrotron SAXS experiments were prepared at lipid and DNA concentrations about 100 times greater then typically used in optical microscopy and transfection studies. SAXS scans of mixtures at typical transfection concentrations, also shown in FIG. 5b, have Bragg peaks at exactly the same positions as in corresponding more concentrated samples. This confirms that the internal $L_\alpha^C$ and $H_{II}^C$ structures of the complexes and the phase boundaries between them are independent of the overall DNA and lipid concentrations.

Figure 6A:
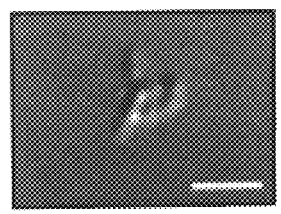
FIGS. 6(A–D) are video-microscopy images of CL-DNA complexes in $H_{II}^C$ and $L_\alpha^C$.
Figure 6A:
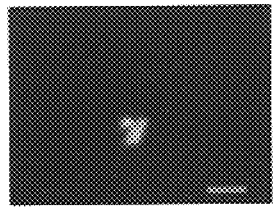
Figure 6A:
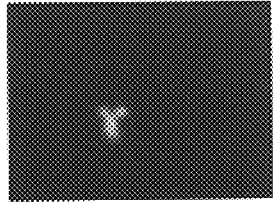
Figure 6B:
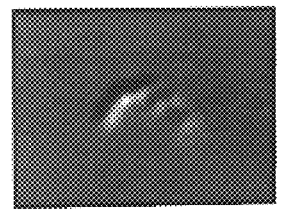
Figure 6B:
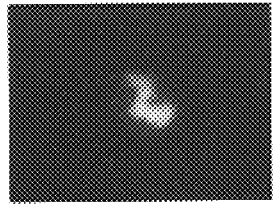
Figure 6B:
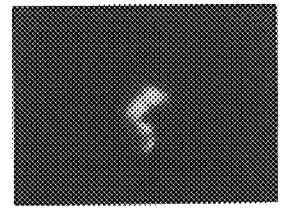

In either of the condensed phases the complexes appear as highly dynamic birefringent aggregates when viewed with video-enhanced optical microscopy (FIGS. 6A, B). Each complex consists of several connected blobs close to charge neutrality, with the aggregates becoming smaller and eventually dissociating into individual blobs with the increasing complex charge. Interestingly, the shape of aggregates is different in the two complex phases: the $L_\alpha^C$ phase forms linear structures, while in the $H_{II}^C$ phase the aggregates are predominantly branched. Microscopy of DNA and lipids with appropriate fluorescent labels allows us to image their respective distributions in the complex. This observations show that the complex is indeed a compact object, with a close association of lipid and DNA, since in both phases the complexes exhibit fluorescence in DNA and lipid modes. The complexes coexist with excess DNA for r<2.2 and with excess lipid when r>2.2. However, we never observe presence of macroscopic lipid aggregates, proving that the only condensed liquid crystalline structures in the CL-DNA mixtures are complexes. On a larger length-scale and at higher lipid and DNA concentrations, bigger LC aggregates are observed (FIG. 6a), with very different defect structures in the two phases. $H_{II}^C$ phase never exhibits the spherrulites characteristic of the $L_\alpha^C$ phase. The spherulites are an unmistaking signature of lamellar liquid-crystalline structure (32), and are not present in hexagonal phases.

Figure 6C:
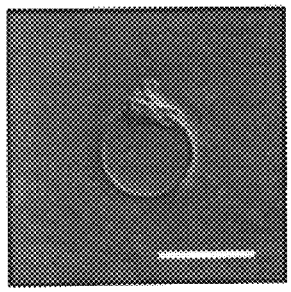
Figure 6C:
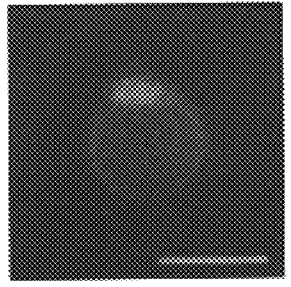
Figure 6C:
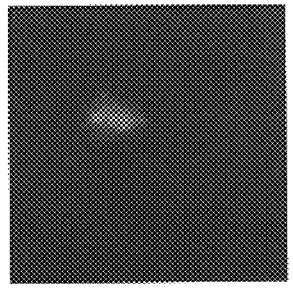
Figure 6D:
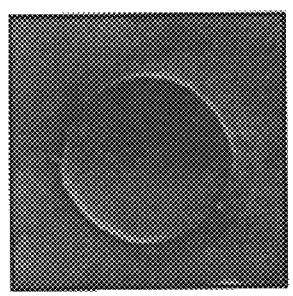
Figure 6D:
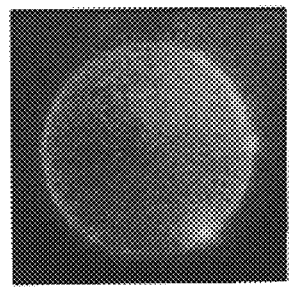
Figure 6D:
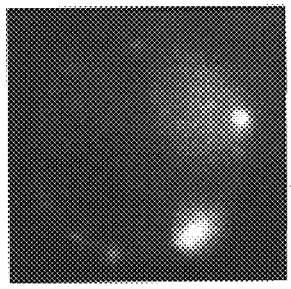

The membrane of giant anionic liposome is a good model of the outer cell membrane—the first barrier to the complex on its way to DNA delivery. There is a striking difference in the way $H_{II}^C$ and $L_\alpha^C$ complexes interact with model anionic lipid membranes. We show in FIG. 6C, D typical micrographs of slightly positively charged (r=4) complexes attached to the fluid membranes of giant liposomes. The $L_\alpha^C$ complexes attached to anionic membrane remain stable for many hours. The compact complex morphology can be seen in DIC as well as in DNA and lipid fluorescence. Clearly there is no fusion between the complex and the giant liposome. A strikingly different behavior is observed with $H_{II}^C$ complexes. They lose their compact structure immediately upon attaching to the liposome, spreading and fusing with it. Since the amount of lipid in the complex is comparable with that in liposome, and since the fusion occurs very quickly, it results in formation of a local multilamellar structure on the giant liposome surface. The loss of the compact complex structure and the subsequent spreading of the DNA fluorescence are clear indications of fusion and the first observed example of the effect of complex structure on its interaction with a membrane. This finding unambiguously demonstrates the importance of complex internal structure for the efficiency of CL-DNA vectors.

Figure 7:
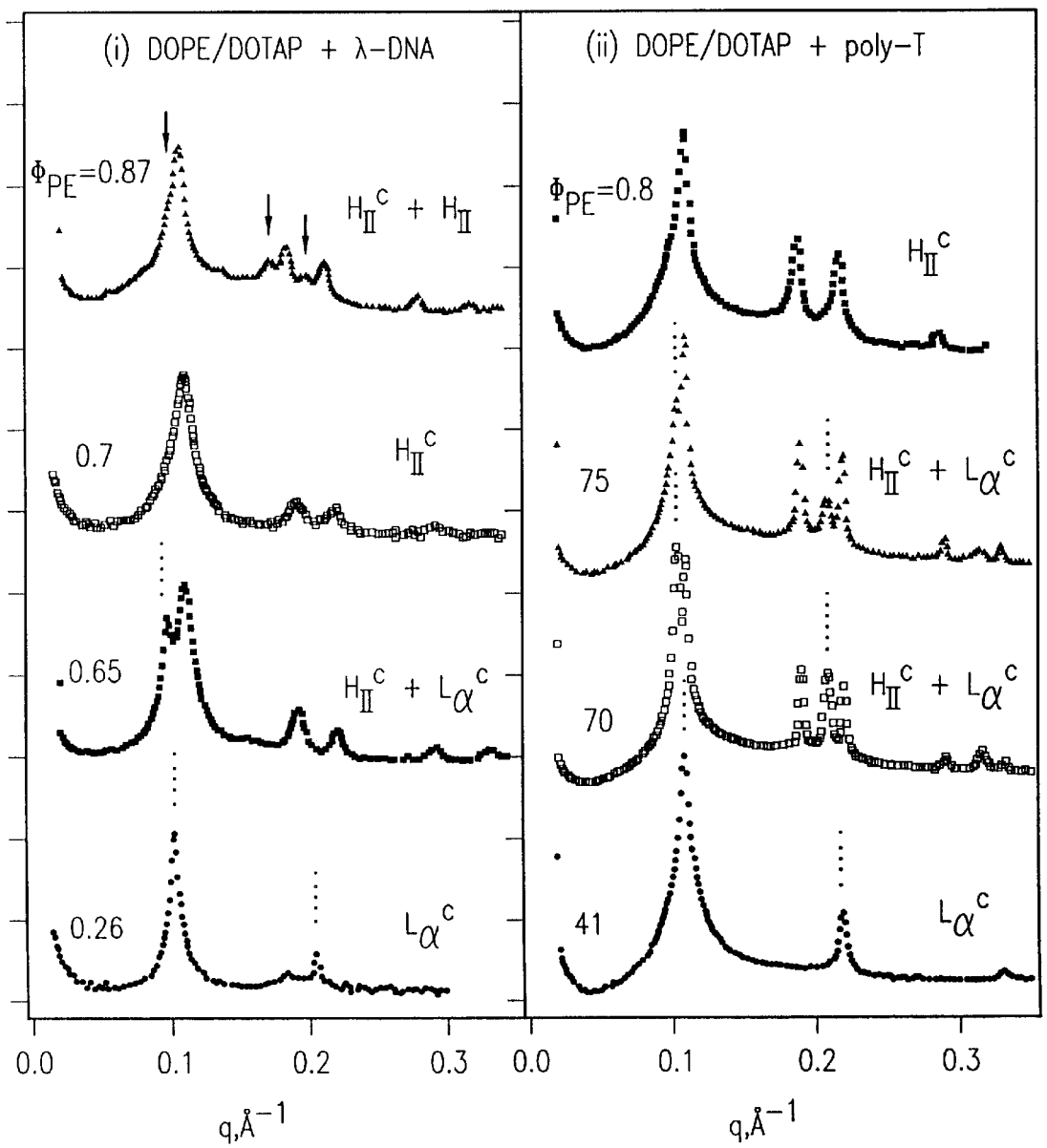
FIG. 7 are two SAXS scans obtained following the transformation from $L_\alpha^C$ to $H_{II}^C$ phase in the case when the macromolecule is DNA (Left) or a polynucleotide T (right).

The presence of $H_{II}^C$ and $L_\alpha^C$ phases is universal in complexes of DOPE/DOTAP mixtures with other anionic polyelectrolytes. FIG. 7 shows SAXS scans of complexes with DNA and oligonucleotide polyT (100 bases long) as a function of $\Phi_{PE}$. As $\Phi_{PE}$ increases, the complexes undergo a first order phase transition from lamellar to hexagonal structure with a broad range of $\Phi_{PE}$ were the two phases coexist. The same structures are also observed in complexes of DOPE/DOTAP with anionic polypeptide PGA (MW=81, 000). The only difference in the structure of complexes between DNA and the shorter polyelectrolytes is the absence of polymer-polymer correlation peak in the $L_\alpha^C$ phase. We attribute this difference to the difference in length and rigidity between very long and stiff DNA and shorter, more flexible polyT and PGA.

Figure 8:
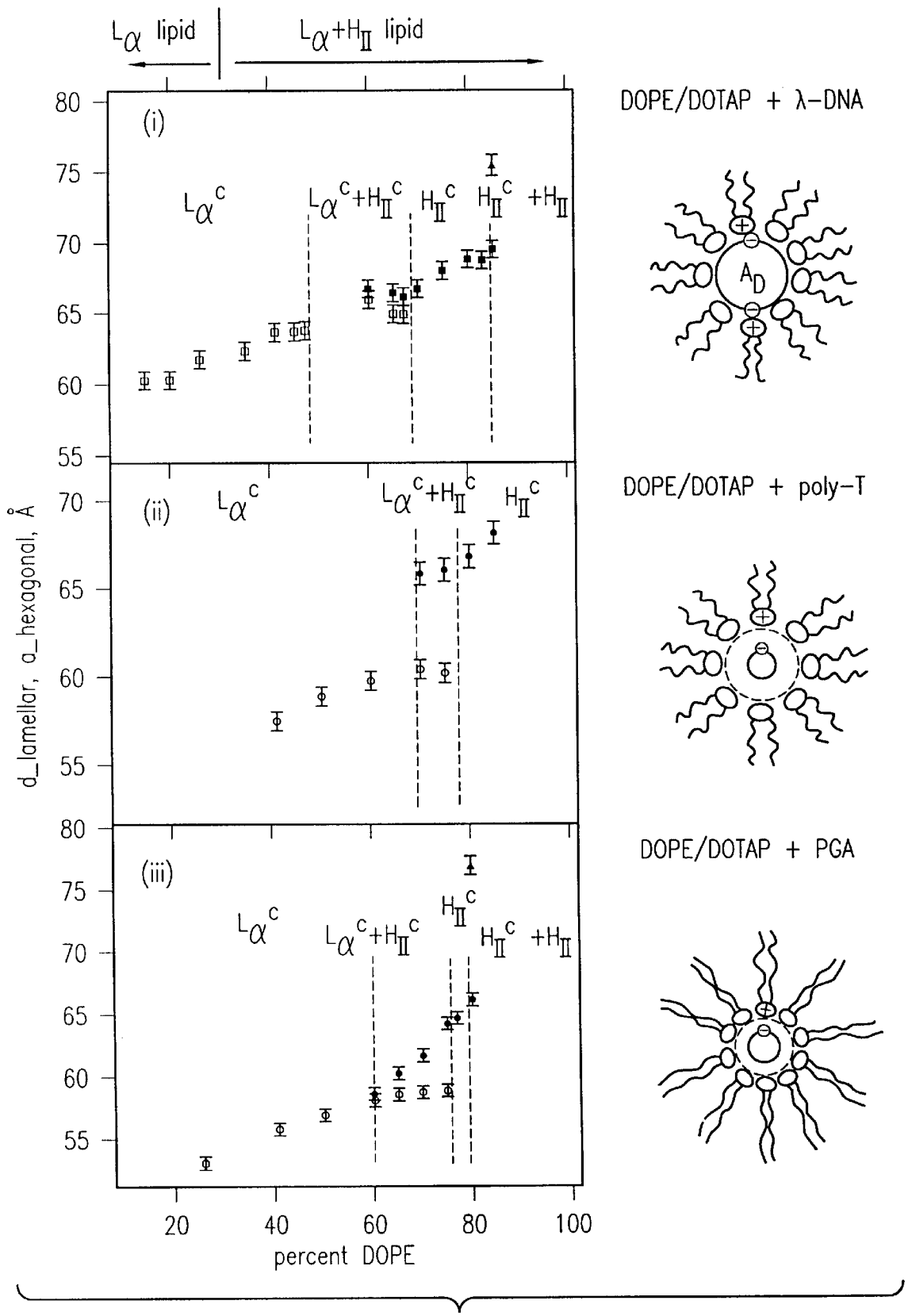
FIG. 8 shows the variation of structural parameters in $L_\alpha^C$ and $H_{II}^C$ complexes with the three different types of polyelectrolytes and correlative schematic diagrams showing the structure of a unit cell in the three $H_{II}^C$ complexes (with DNA, Poly-T, or PGA as the macromolecule).

We compare the phase diagrams of CL-polyelectrolyte complexes for the three different polymers in FIG. 8, which also shows the variation of repeat distances of complex structure as a function of $\Phi_{PE}$. To understand the phase sequence in complexes it is useful to consider structure of DOPE/DOTAP mixtures without the polyelectrolytes. These phase boundaries are indicated on top of FIG. 8. Pure lipids also form lamellar $L_a$ and inverted hexagonal $H_{II}$ structures, although the phase boundaries are very different from CL-polymer systems and the $H_{II}$ phase is only present in coexistence with $L_a$ structure. Therefore the phase sequence in the CL-polyelectrolyte mixtures mimics the ones preferred by the pure lipids, with stabilization of the pure inverted hexagonal phase. DOPE forms stable $H_{II}$ phases, whereas DOTAP has stable lamellar structures. Once the complex is formed and lipid and polymer counterions are released, the internal structure of the complex will be affected by several comparable free energy contributions.

Since DOPE monolayers have negative spontaneous curvature and bending energy of only a few $k_B T^{16}$, increasing $\Phi_{HE}$ will allow the lipid layers to curve around the polyelectrolites, forming the $H_{II}^C$ structure. Additionally, the lipid head-group area and correspondingly chain length will adjust itself so as to further minimize the free energy of the system, since the stretching energy of the lipid chain is only slightly greater then the bending energy of the monolayers. The three polyelectrolites which we have studied have different diameters (20 Å DNA, 13 Å PGA which has a-helix conformation inside the complex, ~10 Å poly-T) and different linear charge densities ($1=2e^-/3.4$ Å DNA, $1e^-/1.5$ Å PGA, $\sim 1e^-/3.4$ Å poly-T). This changes the relative magnitude of electrostatic interaction in the complex, as well as the required amount of lipid monolayer bending in the $H_{II}^C$ phase, thus shifting the phase boundaries and structure of a unit cell in the complex.

Further insight into the relative phase boundaries and structures in the three CL-polymer complexes may be gained if one considers that the charge densities of polyelectrolyte and lipid monolayers have to match within the $H_{II}^C$ unit cell, $$\lambda = \frac{\pi D}{A}(1 - \phi_{PE}),$$

were A is the lipid head-group area and D is the radius of lipid monolayer, which may be larger then polyelectrolyte diameter. Let us assume first that the lipid layer thickness remains fixed at $d_m=40$ Å in the $H_{II}^C$ complex. Then in CL-DNA complex D=24 Å and A=65 Å (normal value), giving $\Phi_{PE}=0.5$, close to experimentally observed lower boundary of the $H_{II}^C$ phase. This implies closely matched diameters of DNA and lipid monolayers in the complex unit cell (FIG. 8). In CL-pT complex D=25 Å and A=65 Å, giving at $\Phi_{PE}=0.75$, again close to the experimentally observed value. This corresponds to a loosely bound unit cell, as shown in FIG. 8. Higher $H_{II}^C$ phase boundary and greater difference between polymer and monolayer diameters arise because of the weaker electrostatic interaction and larger monolayer bending in CL-pT complex compared with CL-DNA. In CL-PGA $H_{II}^C$ phase, a reasonable phase boundary may be only achieved if the head-group area is substantially smaller, resulting in stretching of the lipid chains and increase in lipid layer spacing. With A=40 Å and D=20 Å one obtains $\Phi_{PE}=0.6$, in reasonable agreement with experiment. Here stronger electrostatic interaction and small polymer diameter result in crowding of lipid heads. The additional free energy of stretching the chains may be the cause of the very narrow region of stability of pure $H_{II}^C$ phase in CL-PGA system.

We have provided a first demonstration for the existence of distinctly different lamellar and hexagonal LC structures of CL-DNA complexes. These structures are formed at different lipid compositions and interact differently with model anionic membranes. The two LC phases also form in other Cl-biopolyelectrolyte complexes used for intracellular delivery. Comparison between the complexes in three different systems also improves the understanding of interactions shaping complex structure. This will be important for controlled design of the new class of surfactant-polyelectrolyte materials (46), of which our complexes are examples.

Figure 5B:
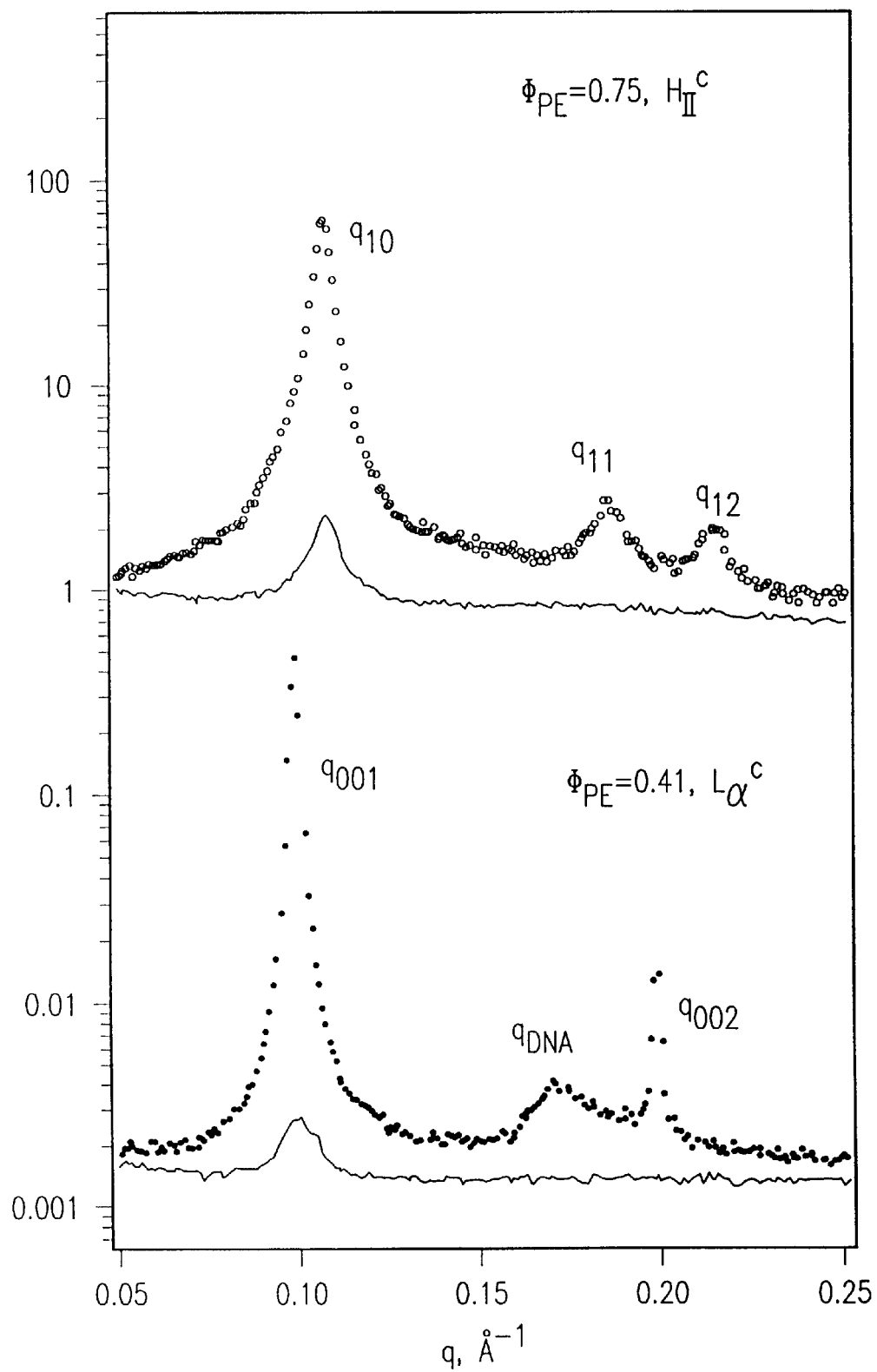
FIG. 5(B) is the powder X-ray diffraction patterns of two distinct ($H_{II}^C$ and $L_\alpha^C$) liquid-crystalline phases of CL-DNA complexes.

FIG. 5(A) shows the schematic of the complex formation from the negatively charged DNA and positively charged liposomes. Complete topological rearrangement of lipids and DNA in this process is driven by release of partially-bound counterions from the diffuse screening layers into bulk solution, which lowers the electrostatic free energy of the system. However, once the counterions are released and the lipids are bound to DNA, the liquid-crystalline structure of the complex will depend on the interplay of various comparable contributions to the complex free energy. These vary with the lipid composition of the complex, resulting in two different observed structures: the lamellar complex $L_\alpha^C$ when the volume fraction of neutral DOPE lipid ($\Phi_{PE}$) is $\Phi_{PE}<0.41$ and the inverted hexagonal complex $H_{II}^C$ for $\Phi_{PE}>0.7$. The two structures coexist for intermediate $\Phi_{PE}$.;

FIG. 5(B) provides the powder X-ray diffraction patterns of the two distinct liquid-crystalline phases of CL-DNA complexes. Scan of the $H_{II}^C$ complex at $\Phi_{PE}=0.75$ (open circles, top) shows the first three order Bragg peaks of the hexagonal DNA/lipid lattice at $q_{10}=0.107$ Å$^{-1}$, $q_{11}=0.185$ Å$^{-1}$ and $q_{20}=0.214$ Å$^{-1}$. Scan of the lamellar $L_\alpha^C$ complex at $\Phi_{PE}0.41$ (filled circles, bottom) shows the peaks at $q_{001}=0.099$ Å$^{-1}$ and $q_{002}=0.198$ Å$^{-1}$ resulting from the lamellar periodic structure with DNA intercalated between lipid bilayers and a peak at $q_{DNA}=0.172$ Å$^{-1}$ due to the smectic structure of the intercalated DNA. In both cases the samples were prepared by mixing concentrated deionized water solutions of DNA (5 mg/ml) and lipid (25 mg/ml) directly in a 1.5 mm diameter quartz x-ray capillary with r=3. Because these concentrations are higher then typically used in preparation of CL-DNA complexes for cell transfection, we have also recorded SAXS patterns of complexes made from dilute DNA (0.01 mg/ml) and lipid (0.1 mg/ml) solutions (solid lines). The peak positions are the same for experiments done with concentrated and dilute complexes, indicating that the complex phases remain the same at lipid and DNA concentrations typically used for cell transfection.

FIGS. 6(A–B) provides video-microscopy images of CL-DNA complexes in (a) $H_{II}^C$ and (b) $L_\alpha^C$ phases. In all cases complexes were viewed in DIC (left), lipid fluorescence (middle) and DNA fluorescence (right). For fluorescence experiments cationic lipids were labeled with 0.2 mol % of DHPE-TexasRed and DNA was labeled with Yo Yo-1 iodide at 1 dye molecule/15 bP ratio: The complex morphology is different in the two phases: branched in the $H_{II}^C$ and linear in the $L_\alpha^C$ phase. In both phases the lipid is closely associated with DNA, as evidenced by the exactly same morphology of complexes in the two fluorescence modes. Complexes were prepared by gently mixing DNA (0.01 mg/ml) and lipid (0.1 mg/ml) stock solutions with $\Phi_{PE}=0.73$ (a) and $\Phi_{PE}=0.3$ (b) to yield the r=3 weight ratio (slightly positively charged complexes). The complexes were further diluted with deionized water for observation. Scale bar is 2 μm in DIC and 4 μm in fluorescence images.

FIGS. 6(C–D) provides video microscopy of positively charged $H_{II}^C$ (c) and $L_\alpha^C$ (d) complexes that interact differently with the negatively charged giant liposomes. The lamellar complexes simply stick to the liposomes and remain stable for many hours, retaining their blob-like morphology. The blobs are localized in DIC as well as lipid and DNA fluorescence modes. The hexagonal complexes break-up and spread immediately after attaching to giant liposomes, indicating a fusion process between the complex and the liposome lipid bilayer. Spreading of the complex is evident in both lipid and DNA fluorescence modes. Giant unilamellar liposomes were prepared from the mixtures of 90% DOPC (neutral) and 10% DOPG (negatively charged) lipids. CL-DNA complexes were prepared as described above with r=4. Scale bar is 10 μm in both DIC and fluorescence images.

FIG. 7 provides SAXS scans following the transformation from $L_\alpha^C$ to $H_{II}^C$ phase with increasing amount of DOPE for complexes with DNA (i) and poly-Thymine (ii). The dashed line indicates $L_\alpha^C$ phase peaks. At very high DOPE content ($\Phi_{PE} > 0.85$) the $H_{II}^C$ complexes coexist with the excess $H_{II}$ phase of pure DOPE (peaks marked with arrows). In both (i) and (ii) r=3, slightly above charge-neutrality.

FIG. 8 shows variation of structural parameters in $L_\alpha^C$ and $H_{II}^C$ complexes with the three different types of polyelectrolytes (i) 1-DNA, (ii) poly-Thymine (polyT), (iii) poly-glutamic acid (PGA). In all cases $a \approx \sqrt{3}/2d$, were a is the repeat distance of pure $H_{II}^C$ and d is the membrane repeat distance in pure $L_\alpha^C$ complex. Thus $L_\alpha^C$ and $H_{II}^C$ phases are always epitaxially matched, but this condition is not satisfied for the regions of phase coexistence. The arrows on top of the figure indicate the phase boundaries in the mixtures of DOPE and DOTAP lipids, indicating that the presence of polyelectrolytes stabilizes the pure lamellar and hexagonal phases. Schematic representations show the structure of a unit cell in the three $H_{II}^C$ complexes, demonstrating that the thickness of water layer and the stretching of the lipid chains should be different in the three polyelectrolyte-lipid complexes.

EXAMPLE 3

Recently we have found that cationic liposomes (CL) complexed with DNA (CL-DNA) form a novel self-assembled structure consisting of a higher ordered multilamellar structure with DNA sandwiched between cationic lipid bilayers shown schematically in FIG. 5. These series of x-ray diffraction experiments lead to the observation of a variation in the DNA interaxial distance as a function of the lipid to DNA (L/D) weight ratio in multilayers which unambiguously showed that the x-ray technique was directly probing the DNA structure in multilayer assemblies. It was found that the linear DNA confined between bilayers forms an expanding one-dimensional lattice of chains with the center to center distance between DNA varying in a controlled manner in the nanometer range 25 Å$<d_{DNA}<$60 Å.

Figure 9:
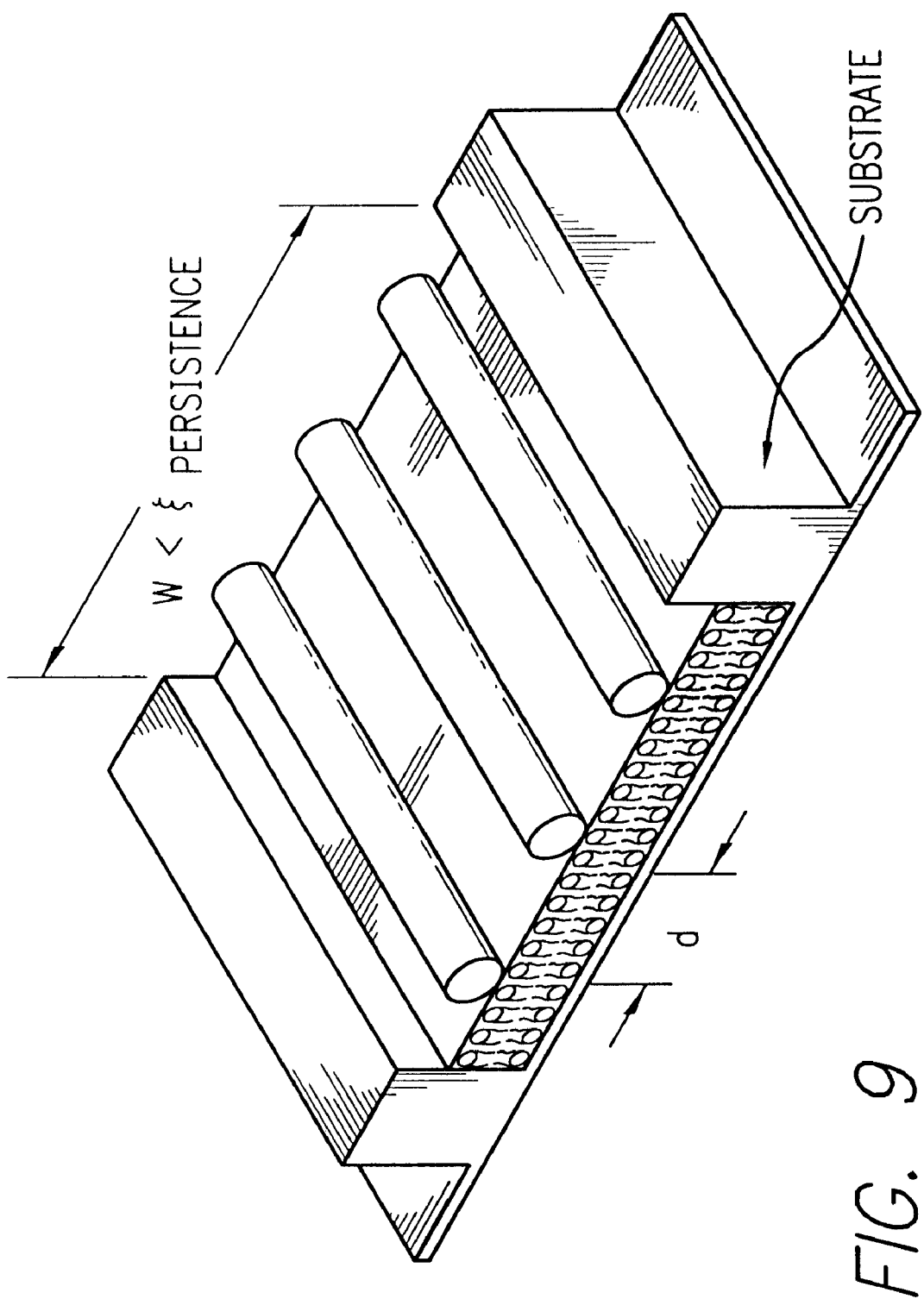
FIG. 9 is a schematic of DNA-lipid complex oriented in microchannels with applications in nanolithograph and separations (or in oriented multilayers).

Microstructures with submicron linewidths as substrates for confining and orienting this multilamellar CL-DNA structure is shown schematically in FIG. 9. The oriented multilamellar structure would have many important technological applications. For example, in developing nano-scale masks in lithography and molecular sieves with nanometer scale cylindrical pores (FIG. 9).

EXAMPLE 4

We have discovered a novel two-dimensional (2D) columnar phase in mixtures of DNA complexes with cationic liposomes (CL) in a concentration regime empirically known to be significantly more efficient at transfecting mammalian cells in culture compared to the lamellar ($L_\alpha^C$) structure of CL-DNA complexes. The structure derived from synchrotron x-ray diffraction consists of DNA coated by cationic lipid monolayers and arranged on a 2D hexagonal lattice ($H_{II}^C$). Two membrane-altering pathways induce the $L_\alpha^C$ to the $H_{II}^C$ transition: one where the spontaneous curvature of the lipid monolayer is driven negative, and another, where the membrane bending rigidity is lowered using a new class of helper-lipids. Significantly, optical microscopy has revealed that in contrast to the non-transfectant $L_\alpha^C$ complexes which bind stably to anionic vesicles (models of cellular membranes), the transfectant $H_{II}^C$ complexes are unstable, rapidly fusing and releasing DNA upon adhering to anionic vesicles. The observations, underscore the importance of structure to "early-stage" gene delivery events, and provide support for a mechanism of DNA escape from anionic endosomal vesicles known to be a major barrier to transfection.

There is now a surge in interest in elucidating the structures in complexes consisting of DNA mixed with oppositely charged cationic liposomes (CLs) (closed bilayer membrane shells of lipid molecules). The interest in complexes arises because they mimic natural viruses in their ability to act as synthetic carriers of extracellular DNA across outer cell membranes and nuclear membranes for gene delivery (47, 48, 49, 50, 51, 52). The principle advantages of nonviral over viral methods for gene delivery include nonimmunicity and, in particular, the potential of transferring large pieces of DNA into cells. This was dramatically demonstrated when the first-generation human artificial chromosome (HAC) of order 10 Mega base pairs was transferred into cells using CLs although extremely inefficiently (53, 54). The low transfection efficiencies (a measure of the efficiency in transferring exogenous DNA into cells and its expression) with nonviral delivery methods results from a poor understanding of transfection-related mechanisms at the molecular and self-assembled levels, including, a general lack of knowledge of structures of CL-DNA complexes, their interactions with cell membranes, and events leading to cell entry and DNA delivery.

It is known that transfection efficiency mediated by mixtures of cationic lipids and so-called neutral "helper-lipids" varies widely and unpredictably (47, 51, 55). The choice of the helper-lipid has been empirically established to be important. For example, transfection of mammalian cells in culture is efficient in mixtures of the univalent cationic lipid DOTAP (dioleoyl trimethylammonium propane) and the neutral helper-lipid DOPE (dioleoyl-phosphadtidylethanolamine), and not in mixtures of DOTAP and a similar helper-lipid DOPC (dioleoyl-phosphatidylcholine) (while DOPE, DOTAP and DOPC were used in this example, one skilled in the art would know that other lipids could be substituted) (56, 57). We demonstrated that DNA mixed with cationic liposomes comprised of DOPC/DOTAP leads to a topological transition into condensed CL-DNA complexes with a multilamellar structure ($L_\alpha^C$) with DNA monolayers sandwiched between cationic lipid bilayers (12) similar to the schematic in FIG. 10 (left).

In this invention, the existence of a completely different columnar inverted hexagonal $H_{II}^C$ liquid-crystalline state in CL-DNA complexes is unambiguously demonstrated for the first time using synchrotron small-angle x-ray diffraction and optical microscopy (FIG. 10; right). We elucidate the role of the commonly used helper-lipid DOPE in inducing the $L_\alpha^C$ to $H_{II}^C$ structural transition by controlling the spontaneous curvature $C_o=1/R_o$ of the lipid monolayer (FIG. 10; pathway I). Further, an entirely new class of helper molecules are introduced which control the membrane bending rigidity κ and give rise to a distinctly different pathway to the $H_{II}^C$ phase (FIG. 10; pathway II). The importance of the precise self-assembled structures to biological function is underscored, first in the demonstration that DOPE containing CL-DNA complexes, which are empirically known to transfect, exhibit the $H_{II}^C$ rather than the $L_\alpha^C$ structure, and second in optical imaging experiments which demonstrate that interactions with model cell membranes mimicking the early stages of transfection are structure-dependent.

We show in FIG. 11(A) synchrotron small angle x-ray scattering (SAXS) scans in positively charged CL-DNA complexes for ρ=DOTAP/DNA (wt./wt.)=3 as a function of increasing $\Phi_{PE}$ (weight fraction of DOPE) in the DOPE/DOTAP cationic liposome mixtures along pathway I. The SAXS experiments were carried out at the Stanford Synchrotron Radiation Laboratory at 8 keV. CL-DNA complexes were prepared by mixing deionized water solutions of highly purified linear λ-phage DNA (5mg/ml; 48502 bp; contour length of 16.5 μm) and cationic liposomes of mixed lipids (25 mg/ml) directly in a 1.5 mm diameter quartz x-ray capillary with ρ=DOTAP/DNA=3 (wt./wt.) which yielded positive complexes. The CLs consisting of binary DOPE/DOTAP mixtures have an average size of 0.06 μm. During the CL-DNA complex formation cationic lipids replace DNA counterions, releasing the Na$^+$ and Cl$^-$ ions into solution with a very large entropic free energy gain (of order $k_BT$ per released counterion). The result is a close association between DNA and lipid in a compact complex with an average size of 0.2 μm size (59).

The complexes are positive for ρ>2.2 and negative for ρ<2.2, indicating that charge reversal occurs when complexes are stoichiometrically neutral with one positive lipid per each negatively charged nucleotide base. We find that the internal structure of the complex changes completely with increasing DOPE/DOTAP ratios. SAXS data of complexes with $\Phi_{PE}$=0.41 and 0.75 clearly shows the presence of two different structures. At $\Phi_{PE}$=0.41, SAXS of the lamellar $L_\alpha^C$ complex (filled circles) shows sharp peaks at $q_{001}$=0.099 Å$^{-1}$ and $q_{002}$=0.198 Å$^{-1}$ resulting from the lamellar periodic structure (d=2 π/$q_{001}$=63.47 Å) with DNA intercalated between cationic lipid (FIG. 10, left). Since the DOPE/DOTAP bilayer thickness at $\Phi_{PE}$=0.41 is $\delta_m$=40 Å (59), the water gap between bilayers $\delta_w$=d-$\delta_m$=23.4 Å is just large enough to accommodate a monolayer of DNA with a hydration shell of water. The middle broad peak at $q_{DNA}$=0.172 Å$^{-1}$ is due to the 1D array of DNA chains with the spacing between the DNA strands $d_{DNA}$=2/$q_{DNA}$. This structure found in CL-DNA complexes with ($\Phi_{PE}$<0.41 is analogous to the one reported in recent studies of the structure and interactions in DOPC/DOTAP-DNA complexes (58, 60).

For 0.7<$\Phi_{PE}$<0.85 the peaks of the SAXS scans of the CL-DNA complexes are indexed perfectly on a two-dimensional (2D) hexagonal lattice with a unit cell spacing of a=4π/[(3)$^{0.5}q_{10}$]=67.4 Å for $\Phi_{PE}$=0.75. We were able to observe Bragg peaks up to the order because of the high brilliance of the synchrotron source, indicating a high degree of regularity of the structure. FIG. 2(A) at $\Phi_{PE}$=0.75 shows the first four order Bragg peaks of this hexagonal structure at $q_{10}$=0.107 Å$^{-1}$, $q_{11}$=0.185 Å$^{-1}$, $q_{20}$=0.214 Å$^{-1}$, and $q_{21}$=0.283 Å$^{-1}$. The structure is consistent with a 2D columnar inverted hexagonal structure shown in FIG. 10 (right) which we refer to as the $H_{II}^C$ phase of CL-DNA complexes. The DNA molecules are surrounded by a lipid monolayer with the DNA/lipid inverted cylindrical micelles arranged on a hexagonal lattice. The structure resembles that of the inverted hexagonal $H_{II}$ phase of pure DOPE in excess water (61), with the water space inside the lipid micelle filled by DNA. The larger electron density of DNA with respect to water leads to the relative suppression of the (57) and (69) Bragg peak intensities compared with that in the lipid $H_{II}$ phase (59). Assuming again an average lipid monolayer thickness of 20 Å, the diameter of micellar void in the $H_{II}^C$ phase is close to 28 Å, again sufficient for a DNA molecule with approximately two hydration shells. For 0.41<$\Phi_{PE}$<0.7 the $L_\alpha^C$ and $H_{II}^C$ structures coexist as shown at $\Phi_{PE}$=0.65 and are nearly epitaxially matched with a~d. For $\Phi_{PE}$>0.85 the $H_{II}^C$ phase coexists with the $H_{II}$ phase of pure DOPE which has peaks at $q_{10}$=0.0975 Å$^{-1}$, $q_{11}$=0.169 Å$^{-1}$, $q_{20}$= 0.195 Å$^{-1}$(arrows in FIG. 11(A) at $\Phi_{PE}$=0.87) with a unit cell spacing of a=74.41 Å.

Figure 11:
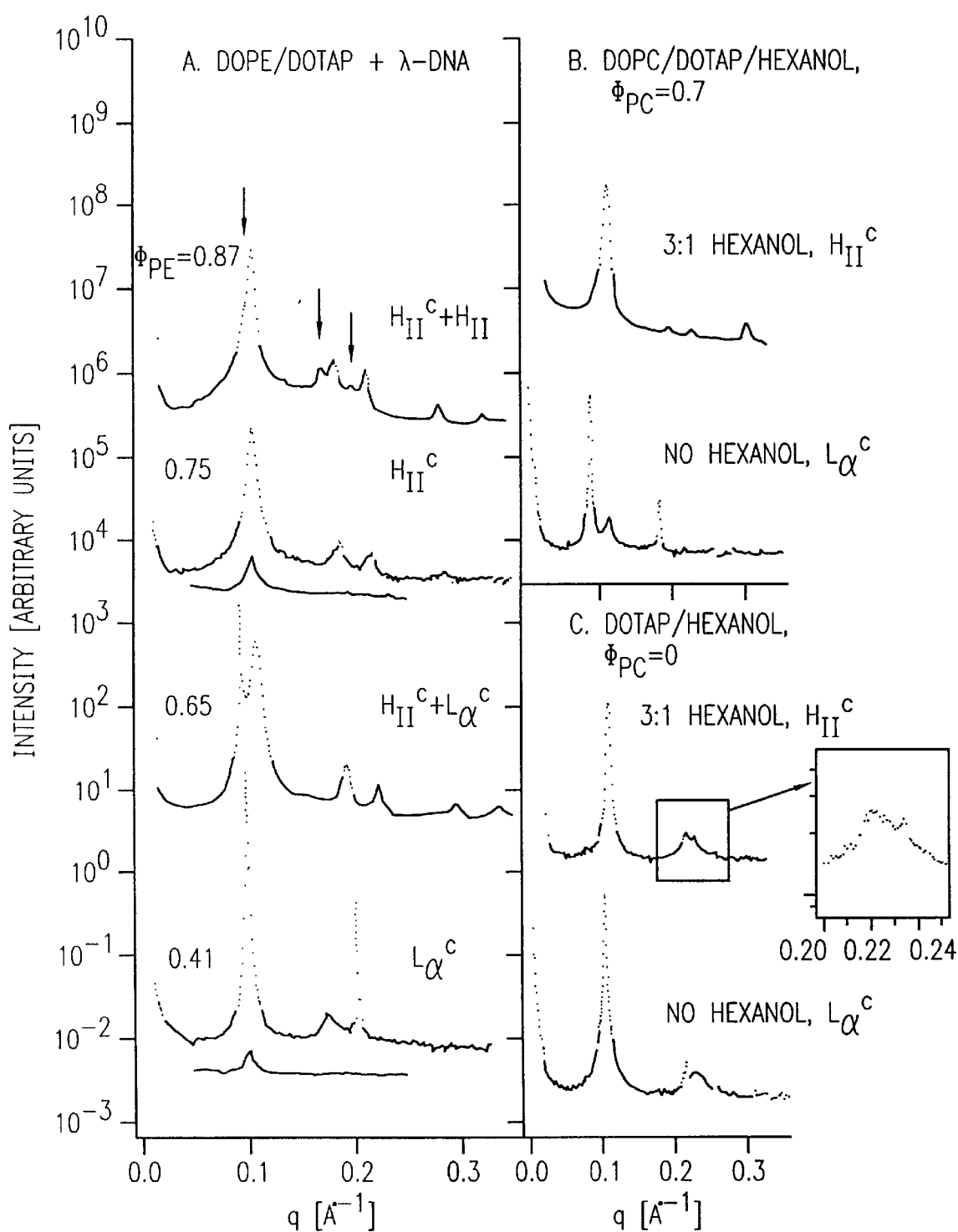
FIG. 11 are Synchrotron SAXS graphs showing the patterns of the lamellar ($L_\alpha^C$) and columnar inverted hexagonal ($H_{II}^C$) phases of positively charged CL-DNA complexes.
Figure 12:
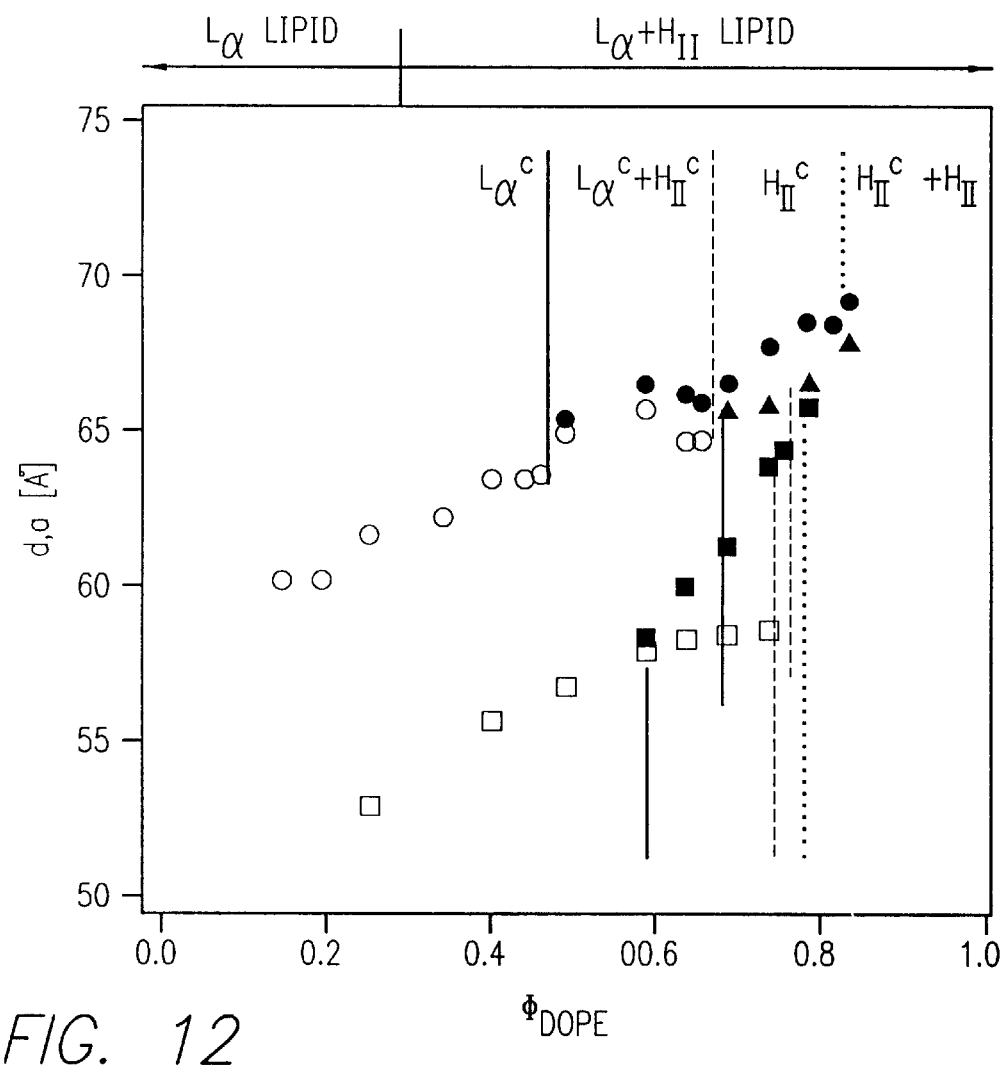
FIG. 12 is a graph representation of the variation of the unit cell parameters in the lamellar ($L_\alpha^C$) and hexagonal ($H_{II}^C$) complexes as a function of $\Phi_{PE}$ in λ-.

We also plot in FIG. 11 (A) at $\Phi_{PE}$=0.41 and 0.75 (solid lines), SAXS scans of CL-DNA complexes at 0.01% concentrations typically used in cell transfection studies (56, 57). We see that the complexes have their first order Bragg peaks at exactly the same positions as in the corresponding more concentrated samples. This demonstrates that in this range of concentrations the internal structures of the complexes are independent of the overall DNA and lipid concentrations. For most of the SAXS experiments we prepared CL-DNA at more concentrated lipid and DNA concentrations (~1%) to improve the signal/background intensity ratio. These mixtures appear as aggregates of the individual complexes shown in FIGS. 13(A and B) and retain a similar globular morphology.

The $L_\alpha^C$ to $H_{II}^C$ phase transition can be induced along a second pathway II (FIG. 10) by the use of a novel new "helper-lipid mixture" that we introduce in this invention. To demonstrate this pathway we consider complexes containing mixtures of DOPC and DOTAP which are always found to exhibit the lamellar $L_\alpha^C$ structure (12) as the SAXS scan shows in FIG. 11(B) (bottom; $\Phi_{PE}$=0.7) with an interlayer spacing of d=2π/$q_{001}$=66.84 Å. As a function of increasing hexanol, a membrane soluble co-surfactant, to the helper-lipid DOPC we find a structural transition to the $H_{II}^C$ phase. This is shown in SAXS scans of complexes containing DOPC/DOTAP/hexanol (($\Phi_{PE}$=0.7, mole ratio of hexanol to total lipid is 3:1) where the first four diffraction peaks (01), (11), (20), and (21) of the hexagonal lattice are clearly indexed with a unit cell size a=62.54 Å. In FIG. 11(C) we find that in CL-DNA complexes of pure cationic lipid DOTAP the addition of hexanol does not induce the transition and we always find the $L_\alpha^C$ structure. In this case, the only effect of the addition of hexanol is to thin the cationic bilayer membrane (consisting of hexanol:DOTAP at a 3:1 mole ratio) from d=57.91 Å to d=54.17 Å. The interaxial DNA-DNA spacing is also observed to increase from $d_{DNA}$= 27.1 Å to 28.82 Å consistent with a decrease in the membrane charge density with the addition of hexanol.

To understand the $L_\alpha^C$ to $H_{II}^C$ transition qualitatively along the two pathways (I and II of FIG. 10) we consider the interplay between the electrostatic and membrane elastic interactions in the complexes. Pure electrostatic interactions alone are expected to favor the $H_\alpha^C$ phase which minimizes the charge separation between the anionic groups on the DNA chain and the cationic lipids (47, 62). The electrostatic interaction may be resisted by the Helfrich elastic cost (per unit area) of forming a cylindrical monolayer membrane around DNA:

$$F/A = 0.5\kappa(1/R - 1/R_o)^2 \tag{1}$$

Here, κ is the lipid monolayer rigidity, R the radius of curvature, and $R_o$ the natural radius of curvature. Along pathway I (FIG. 10) the membrane consists of the two components DOTAP and DOPE. Cationic DOTAP has a natural (also referred to herein as spontaneous) curvature $C_o^{DOTAP}$=1/$R_o^{DOTAP}$=0; that is, membranes of pure DOTAP are known to favor the lamellar $L_\alpha$phase. However, DOPE has a negative natural curvature $C_o^{DOPE}$=1/$R_o^{DOPE}$<0; that is, DOPE has a larger area per 2 chains than area per head group (FIG. 10 center top). Pure DOPE in water forms the inverted hexagonal $H_{II}$, phase (61). Thus, along pathway I the natural curvature of the monolayer mixture of DOTAP and DOPE is driven negative with $C_o$=1/$R_o$=$\Phi_{PE}^V C_o^{DOPE}$, where $\Phi_{PE}^V$ is the volume fraction of DOPE in the lipid mixture monolayer. Hence, as a function of increasing $\Phi_{PE}$ we expect a softening of the elastic cost of monolayer deformation and the transition to the $H_{II}^C$ phase favored by the electrostatic interactions as observed experimentally (FIG. 11(A)).

Pathway II (FIG. 10) involves a subtle mechanism and introduces an entirely new class of helper-lipids to the field of nonviral gene therapy. Along this pathway the membrane bending rigidity κ is reduced significantly because of the addition of the membrane-soluble cosurfactant molecule hexanol. Cosurfactant molecules, while not able to stabilize an interface separating hydrophobic and hydrophilic regions, when mixed in with longer chain "true" surfactants can lead to dramatic changes in interface elasticities. Experimental studies have shown that the addition of hexanol to membranes of lamellar phases with a mole ratio of between two to four will lead to a significant decrease of the bending rigidity κ from ≈20$k_B$T to between 2 to 5 $k_B$T (63). Simple compressional models of surfactant chains show that κ scales with chain length $l_n$ ($\delta_m$, membrane thickness, n=number of carbons per chain) and the area per lipid chain $A_L$ as κ $l_n^3/A_L^5$ (64). Hexanol affects both $l_n$ and $A_L$ shown schematically in FIG. 10 (center bottom). First, the membrane thickness $\delta_m$ decreases upon addition of the shorter tail cosurfactant molecule hexanol ($C_6$ chain) to the mixture of DOPC and DOTAP ($C_{18}$ chains). Second, the addition of a significant amount of short hexanol chains to the long chains (from DOPC and DOTAP) effectively results in a sudden excess free volume and significantly larger area per lipid chain. This will lead to a further strong suppression of κ making the membrane highly flexible. Thus, we expect a reduction of the elastic cost (determined by (1)) of curving the membrane due to the reduction of κ to lead to the formation of the $H_{II}^C$ phase favored by the electrostatic interactions. This was observed experimentally (FIG. 11(B), open squares). We have further observed that the transition to the $H_{II}^C$ phase along pathway II occurs only in CL-DNA complexes with low enough charge density DOTAP/DOPC<0.5 (59). FIG. 11(C) shows SAXS data in this regime where the $L_\alpha^C$ structure is retained in complexes with pure DOTAP with and without added hexanol consistent with theory which predicts a renormalized increase in κ with increasing surface charge density (65).

It is important to note that in the absence of DNA, lipids formed from a mixture of DOPC and DOTAP with or without hexanol form stable lamellar $L_\alpha^C$ phases (with $C_o$=0) in the lipid mixtures studied in this work with no tendency of forming the inverted $H_{II}$ phase (59). This then is a clear distinction between the two classes of helper-lipids used along the two pathways where DOPE/DOTAP/water mixtures do form coexisting $H_{II}^C$ and $L_\alpha^C$ phases.

We demonstrate the generality of the lamellar $L_\alpha^C$ to hexagonal $H_{II}^C$ transformation by observing it in complexes of DOPE/DOTAP mixtures with two other negatively charged polyelectrolytes-polyglutamic acid (PGA), a model polypeptide, and poly-thymine (poly-T), a model of single-stranded oligo-nucleotides which are used in antisense delivery applications (66, 67). The phase diagram of CL-polyelectrolyte complexes is plotted in FIG. 12 showing the variation of the unit cell parameters in the $L_\alpha^C$ and $H_{II}^C$ complexes as a function of $\Phi_{PE}$ for DNA, a 100 bp poly-T, and PGA. The phase sequence in DOPE/DOTAP mixtures without the polyelectrolytes is indicated at the top by horizontal arrows. Pure lipids also form $L_a$ and $H_{II}$ structures, although, the $H_{II}$ is present only in coexistence with the $L_\alpha$phase which indicates that the polyelectrolytes stabilize the $H_{II}^C$ single phase. The observed different phase boundaries most likely originate from differences in diameter and linear charge density between the ployelectrolytes which in turn leads to different required amounts of lipid monolayer bending around the polyelectrolyte in the $H_{II}^C$ complex. This demonstrates the interplay between electrostatics and membrane elasticities in these hybrid systems (59).

Figure 13A:
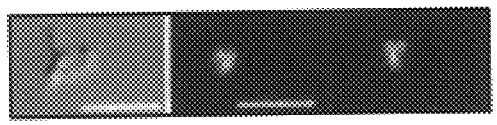
FIGS. 13 (A–D) are video-microscopy image of positively charged CL-DNA complexes in the $H_{II}^C$ (a) and $L_\alpha^C$ (b) phases, viewed in Differential-Interference-Contrast (DIC) (left), lipid fluorescence (middle), and DNA fluorescence (right).
Figure 13B:
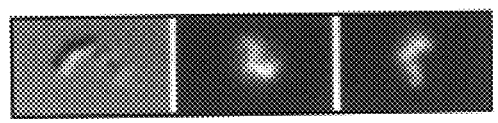

In both condensed phases the complexes appear as highly dynamic birefringent aggregates when viewed with video-enhanced optical microscopy in differential-interference-contrast (DIC) and fluorescence configurations as shown in FIG. 13(A) for $H_{II}^C$ ($\Phi_{PE}$=0.73) and FIG. 13(B) for $L_\alpha^C$ ($\Phi_{PE}$=0.3) complexes along pathway I. For fluorescence experiments cationic lipids were labeled with 0.2 mol % of DHPE-TexasRed and DNA was labeled with YoYo-1 iodide at a 1 dye molecule/15 bP ratio. Complexes were prepared by gently mixing DNA (0.01 mg/ml) and lipid (0.1 mg/ml) stock solutions. The complexes were further diluted with deionized water for observation. Giant unilamellar vesicles were prepared from mixtures of 90% DOPC (neutral) and 10% DOPG (negatively charged) lipids. Positively charged CL-DNA complexes were prepared. The SAXS experiments were carried out at the Stanford Synchrotron Radiation Laboratory at 8 keV. CL-DNA complexes were prepared by mixing deionized water solutions of highly purified linear λ-phage DNA (5 mg/ml; 48502 bp; contour length of 16.5 μm) and cationic liposomes of mixed lipids (25 mg/ml) directly in a 1.5 mm diameter quartz x-ray capillary with ρ=DOTAP/DNA=3 (wt./wt.) which yielded positive complexes. The CLs consisting of binary DOPE/DOTAP mixtures have an average size of 0.06 μm. During the CL-DNA complex formation cationic lipids replace DNA counterions, releasing the Na$^+$and Cl$^-$ions into solution with a very large entropic free energy gain (of order $k_B$T per released counterion). The result is a close association between DNA and lipid in a compact complex with an average size of 0.2 μm size (59).

The positive complexes (with ρ=3) are seen to form aggregates consisting of connected blobs with the aggregates becoming smaller and eventually dissociating into individual blobs with increasing complex charge. Interestingly, the shape of aggregates is different in the two complex phases: the $L_\alpha^C$ phase forms linear structures, while in the $H_{II}^C$ phase the aggregates are predominantly branched indicating an inherent anisotropic shape to the $H_{II}^C$ complexes (59). FIG. 13(A) shows the distribution of Lipid fluorescence (middle) and DNA fluorescence (right) in the same CL-DNA complex in the $H_{II}^C$ phase and FIG. 13(B) shows it for a CL-DNA complex in the $L_\alpha^C$ phase. The observed overlap of lipid and DNA distributions and the precisely identical morphologies in the two fluorescence modes shows that the complexes are indeed highly compact objects with a close association of lipid and DNA consistent with the SAXS data of these extremely dilute samples (FIG. 11(A)). At these concentrations and volume fractions of DOPE the complexes coexist with excess DNA for ρ<2.2 and with excess lipid when ρ>2.2 and we have not observed the presence of macroscopic lipid aggregates, which indicates that the only condensed liquid crystalline structures in the CL-DNA mixtures are complexes.

To understand the effect of structure on the early stages of transfection we studied the interaction of CL-DNA complexes with giant anionic vesicles (G-vesicles) which are models of CL-DNA complex—anionic endosomal vesicles of cells. Experiments indicate that the main entry route to mammalian cells is endocytosis where a local inward deformation of the cell plasma membrane leads to budding off of an internal vesicle forming the early stage endosome (68, 69, 70, 71). Thus, at the early stages of cell transfection, an intact CL-DNA complex is captured inside an endosomal vesicle which is anionic due to the anionic lipids of the plasma membrane.

There is a striking difference between positively charged $H_{II}^C$ and $L_\alpha^C$ complexes in their interaction with model anionic lipid membranes even when both types of structures contain DOPE. We show in FIGS. 13(C and D) typical micrographs of positively charged ($\rho$=4) complexes attached to the fluid membranes of G-vesicles. The $L_\alpha^C$ complexes attach to the G-vesicles and remain stable (C). The compact complex morphology can be seen in DIC (left) as well as in the lipid (C, middle) and DNA (C, right) fluorescence. Clearly there is no fusion between the complex and the G-vesicle. $H_{II}^C$ complexes behave dramatically differently upon attaching to the G-vesicle, rapidly fusing and spreading with it and losing their compact structure (FIG. 13(D), left, DIC). Since the amount of lipid in the complex is comparable with that in the G-vesicle, and since the fusion occurs very quickly, it results in the formation of multiple free lamella which are observed to undergo bilayer fluctuations. The loss of the compact complex structure and the subsequent desorption of DNA molecules from membrane and their brownian motion between the lamella are seen in fluorescence (FIG. 13(D), right). This behavior is expected following fusion which results in the mixing of cationic-lipid (from the $H_{II}^C$ complex) with anionic lipid (from the G-vesicle) effectively "turning off" the electrostatic interactions (which gave rise to the compact CL-DNA complexes) and releasing of DNA molecules inside the space between the lamellae and the G-vesicle bilayer. Since the geometry is the inverse of CL-DNA complexes inside anionic endosomal vesicles an expected result is that upon fusion the inverse geometry will occur with DNA released and expelled outside the endosome within the cytoplasm. Fluorescence microscopy studies show similar behavior in mouse fibroblast cell cultures where $L_\alpha^C$ complexes appear intact in the cell for two hours after endocytic uptake, whereas, $H_{II}^C$ complexes show fusion after endocytic uptake.

The findings unambiguously establish a correlation between the self-assembled structure of CL-DNA complexes and transfection efficiency: the empirically established transfectant complexes in mammalian cell cultures exhibit the $H_{II}^C$ structure rather than the $L_\alpha^C$. The reported behavior is in complexes containing univalent cationic lipids; multivalent cationic lipids may behave differently. Further, optical microscopy reveals a most likely origin for why different structures transfect cells with varying efficiency: in contrast to $L_\alpha^C$ complexes, $H_{II}^C$ complexes are found to fuse and release DNA when in contact with anionic vesicles which are cell free models of cellular organelle membranes, in particular, anionic endosomal vesicles. Thus, the data suggest a simple direct mechanism of DNA release into the cytoplasm from endosomal vesicles containing $H_{II}^C$ complexes. This then paves the way for a fundamental understanding of the early-stage events following the endocytic uptake of CL-DNA complexes by mammalian cells in nonviral gene delivery applications.

FIG. 10 shows a schematic of two distinct pathways from the lamellar $L_\alpha^C$ phase to the columnar inverted hexagonal $H_{II}^C$ phase of cationic liposome-DNA (CL-DNA) complexes. Along Pathway I the natural curvature ($C_o=1/R_o$) of the cationic lipid monolayer is driven negative by the addition of the helper-lipid DOPE. This is shown schematically (middle top) where the cationic lipid DOTAP is cylindrically shaped while DOPE is cone-like leading to the negative curvature. Along pathway II the $L_\alpha^C$ to $H_{II}^C$ transition is induced by the addition of a new class of helper-lipids consisting of mixtures of DOPC and the cosurfactant hexanol which reduces the membrane bending rigidity.

FIG. 11 shows synchrotron SAXS patterns of the lamellar $L_\alpha^C$ and columnar inverted hexagonal $H_{II}^C$ phases of positively charged CL-DNA complexes. FIG. 11(A) shows SAXS scans of CL-DNA complexes as a function of increasing weight fraction $\Phi_{PE}$(=DOPE/[DOPE+DOTAP]) along pathway I of FIG. 10. At $\Phi_{PE}$=0.41, the SAXS results from a single phase with the lamellar $L_\alpha^C$ structure shown in FIG. 10 (left). At $\Phi_{PE}$=0.75, the SAXS scan results from a single phase with the columnar inverted hexagonal $H_{II}^C$ structure shown in FIG. 10 (right). At $\Phi_{PE}$=0.65, the SAXS shows coexistence of the $L_\alpha^C$ (dotted line) and $H_{II}^C$ phases. At $\Phi_{PE}$=0.87, the SAXS shows coexistence of the $H_{II}^C$ phase and the inverted hexagonal $H_{II}$ phase of pure DOPE (Arrows). SAXS patterns of complexes made from extremely dilute DNA (0.01 mg/ml) and lipid (0.1 mg/ml) solutions are plotted as solid lines for $\Phi_{PE}$=0.41 and 0.75. FIG. 10(B) shows SAXS scans of CL-DNA at a constant DOPC weight fraction $\Phi_{PC}$(=DOPC/[DOPC+DOTAP]) with no hexanol (a co-surfactant) and at a hexanol to total lipid mole ratio of 3:1 along pathway II of FIG. 10. With no hexanol (filled squares), the structure is lamellar $L_\alpha^C$ whereas the complexes with hexanol (open squares) exhibit the hexagonal $H_{II}^C$ structure. FIG. 10(C) shows SAXS scans of CL-DNA complexes with DOPC weight fraction $\Phi_{PC}$=0. The complexes remain in the $L_\alpha^C$ phase with and without added hexanol.

FIG. 12 shows variation of the unit cell parameters in the lamellar $L_\alpha^C$ (open symbols denote the interlayer spacing d) and hexagonal $H_{II}^C$ (filled symbols denote the hexagonal unit cell dimension a) complexes as a function of $\Phi_{PE}$ in $\lambda$-DNA (circles, open and filled), poly-Thymine (triangles, open and filled), and polyglutamic acid (squares, open and filled; PGAtween dashed and dotted lines), the coexisting $L_\alpha^C$ and $H_{II}^C$ (between the solid and dashed lines), and $H_{II}^C$ and $H_{II}$ regimes (beyond dotted lines). The arrows on top of the figure indicate the phase boundaries in the lamellar phase in mixtures of DOPE and DOTAP.

Figure 13C:
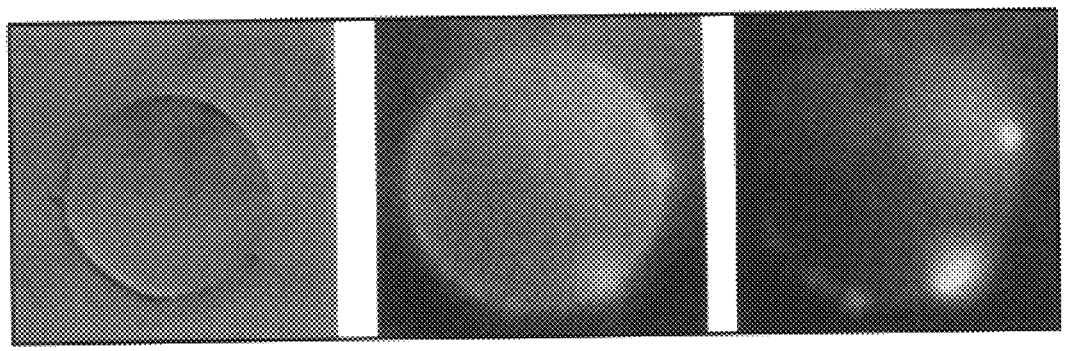
Figure 13D:
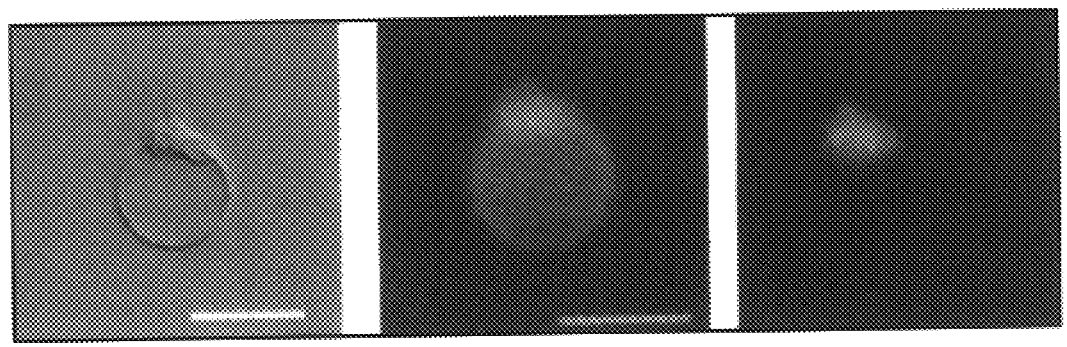

FIG. 13(A), and (B) show video-microscopy images of positively charged CL-DNA complexes in the $H_{II}^C$ (A) and $L_\alpha^C$ (B) phases. In all cases complexes were viewed in Differential-Interference-Contrast (DIC) (left), lipid fluorescence (middle), and DNA fluorescence (right). Scale bar is 3 $\mu$m in DIC and 6 $\mu$m in fluorescence images. FIG. 13(C), and (D) show positively charged $H_{II}^C$ and $L_\alpha^C$ complexes interact differently with the negatively charged giant vesicles (G-vesicles). The $L_\alpha^C$ complexes simply stick to the G-vesicle and remain stable for many hours, retaining their blob-like morphology (C). The blobs are localized in DIC as well as lipid and DNA fluorescence modes. The $H_{II}^C$ complexes break-up and spread immediately after attaching to G-vesicles, indicating a fusion process between the complex and the vesicle lipid bilayer (D). The loss of the compact structure of the complex is evident in both lipid and DNA fluorescence modes. Scale bar is 20 $\mu$m in both DIC and fluorescence images.

REFERENCES

1. R. G. Crystal, Science 270, 404 (1995); R. C. Mulligan, Science 260, 926 (1993).
2. P. L. Felgner, G. Rhodes, Nature 349, 351 (1991).
3. P. L. Felgner, et al., Proc. Natl. Acad. Sci. USA 84, 7413 (1987).

4. N. Zhu, D. Liggitt, Y. Liu, R. Debs, *Science* 261, 209 (1993).
5. G. J. Nabel, et al., *Proc. Natl. Acad. Sci. USA* 90, 11307 (1993); N. M. Caplen, et al., *Nature Medicine* 1, 39 (1995).
6. D. Lasic, N. S. Templeton, *Advanced Drug Delivery Review*, (in press).
7. E. Marshall, *Science* 269, 1050 (1995); E. Marshall, *Science* 270, 1751 (1995).
8. V. A. Bloomfield, *Biopolymers* 31, 1471 (1991).
9. F. Livolant, A. M. Levelut, J. Doucet, J. P. Benoit, *Nature* 339, 724 (1989).
10. Z. Reich, E. J. Wachtel, A. Minsky, *Science* 264, 1460 (1994).
11. E. Sackmann, *Science* 271, 43 (1996); C. Ligoure, G. Bouglet, G. Porte, *Physical Review Letters* 71, 3600 (1993).
12. H. E. Warriner, S. H. J. Idziak, N. L. Slack, P. Davidson, C. R. Safinya, *Science* 271, 969 (1996); A. K. Kemworthy, K. Hristova, D. Needham, T. J. McIntosh, *Biophysical J.* 68, 1921 (1995).
13. H. Gershon, R. Ghirlando, G. S. B., A. Minsky, *Biochemistry* 32, 7143 (1993).
14. J. Gustafsson, G. Arvidson, G. Karlsson, M. Almgren, *BBA* 1235, 305 (1995).
15. B. Sternberg, F. L. Sorgi, L. Huang, *FEBS letters* 356, 361 (1994).
16. S. B. Smith, L. Finzi, C. Bustamante, *Science* 258, 1122 (1992); T. T. Perkins, E. S. Douglas, S. Chu, *Science* 264, 819 (1994).
17. J. P. Behr, *Bioconjugate Chemistry* 5, 382 (1994).
18. A. Singhal, L. Huang, *Gene Therapeutics. Methods and Applications of Direct Gene Transfer.* J. A. Wolff, Ed., (Birkhauser, Boston 1994).
19. Felgner, J., et al. *J. Biol.Chem.* 269, 2550–2561 (1994).
20. Remy, J. -S., Sirlin, C., Vierling, P. & Behr, J. -P. *Bioconjugate Chem.* 5, 647–654 (1994).
21. Raedler, J. O. et al. *Science* 275, 810–8 (1997).
22. Farhood, H., Serbina, N. & Huang, L. *Biochim.Biophys. Acta* 1235, 289–295 (1995).
23. Hui, S. W., et al. *Biophys. J.* 71, 590–599 (1996).
24. Raedler, J. O. et al. *Science* 275, 810–8 (1997).
25. Chiang, M.-Y., et al. *J Biol.Chem.* 266, 18162–18171 (1991).
26. D. Roux, C. R. Safinya, *J. Physique France* 46, 307 (1988).
27. C. R. Safinya, in *Phase Transitions in Soft Condensed Matter* R. Tormod, D. Sherrington, Eds. (Plenum, N.Y., 1989) pp. 249–270.
28. R. Podgornik, D. C. Rau, V. A. Parsegian, *Macromolecules* 22, 1780 (1989).
29. Lappalainen, K., et al. *Biochim.Biophys.Acta* 1196, 201–208 (1994).
30. G. S. Manning, *Journal of Chemical Physics* 51, 924 (1969).
31. P. Boltenhagen, O. D. Lavrentotovich, M. Kleman, *Phys. Rev. A* 46, 1743 (1992).
32. Seddon, J. M. *Biochim.Biophys.Acta* 1031, 1–69 (1989).
33. Boltenhagen, P., Lavrentovich, O. D. & Kleman, M. *Phys.Rev. A* 46, 1743–1746 (1992).
34. J. V. Selinger, R. F. Bruinsma, *Physical Review A* 43, 2922 (1991).
35. W. Helfrich, Z *Naturforsch A* 33, 305 (1978).
36. C. R. Safinya, et al., *Physical Review Letters* 57, 2718 (1986).
37. E. A. Evans, V. A. Parsegian, *Proceedings of the National Academy of Sciences U.S.A.* 83, 7132 (1986).
38. N. Dan, *Biophysical Journal* (in press).
39. Kamien, D. R. Nelson, *Phys. Rev. E* 53, 650 (1996).
40. Behr, J. -P. *Bioconjugate Chem.* 5, 382–389 (1994).
41. Raedler, J. O., Koltover, I., Salditt, T., Safinya, C. R. *Science* 275, 810–814 (1997).
42. Felgner, P. L., et al. *Proc.Natl.Acad.Sci. USA* 84, 7413 (1987).
43. Remy, J. -S., Kichler, A., Mordinov, V., Schuber, F. & Behr, J. -P. *Proc.Natl.Acad.Sci. USA* 92, 1744–1748 (1995).
44. Zhu, N., Liggitt, D., Yong, L. & Debs, R. *Science* 261, 209–211 (1993).
45. Gruner, S. M. *J.Phys.Chem.* 93, 7562–7570 (1989).
46. Antonietti, M., Conrad, J. & Thunemann, A. *Macromolecules* 27, 6007–6011 (1994).
47. P. L. Felgner, *Scientific American* 276, 102 (1997).
48. T. Friedmann, *Scientif American* 276, 96 (1997).
49. P. L. Felgner, G. Rhodes, *Nature* 349, 351 (1991).
50. J. -P. Behr, *Bioconjugate Chem.* 5, 382 (1994).
51. J. -S. Remy, C. Sirlin, P. Vierling, J. -P. Behr, *Bioconjugate Chem.* 5, 647 (1994).
52. N. Zhu, D. Liggitt, L. Yong, R. Debs, *Science* 261, 209 (1993).
53. J. J. Harrington, G. VanBokkelen, R. W. Mays, K. Gustashaw, H. F. Willard, *Nature Genetics* 272, 21994 (1997).
54. W. Roush, *Science* 276, 38 (1997).
55. J. Felgner, et al., *J. Biol.Chem.* 269, 2550 (1994).
56. H. Farhood, N. Serbina, L. Huang, *Biochim.Biophys. Acta* 1235, 289 (1995).
57. S. W. Hui, et al., *Biophys.J.* 71, 590 (1996).
58. J. O. Raedler, Koltover, I., Salditt, T., Safinya, C. R., *Science* 275, 810 (1997).
59. I. Koltover, T. Salditt, C. R. Safinya, unpublished results.
60. T. Salditt, I. Koltover, J. O. Raedler, C. R. Safinya, *Physical Review Letters* 79, 2582 (1997).
61. J. M. Seddon, *Biochim.Biophys.Acta* 1031, 1 (1989).
62. S. May, A. Ben-Shaul, *Biophysical J.* 73, 2427 (1997).
63. C. R. Safinya, E. B. Sirota, D. Roux, G. S. Smith, *Physical Review Letters* 62, 1134 (1989).
64. I. Szleifer, A. Ben-Shaul, W. M. Gelbart, *J. Phys. Chem.* 94, 5081 (1990).
65. G. D. Guttman, D. Andelman, *J. Phys. II France* 3, 1411 (1993).
66. M. -Y. Chiang, et al., *J.Biol.Chem.* 266, 18162 (1991).
67. K. Lappalainen, et al., *Biochim.Biophys.Acta* 1196, 201 (1994).
68. J. Zabner, A. J. Fasbender, T. Moninger, K. A. Poelinger, M. J. Welsh, *J. Biol. Chem.* 270, 18997 (1995).
69. I. Wrobel, D. Collins, *Biochim. Biophys. Acta* 1235, 296 (1995).
70. J. Y. Legendre, F. C. Szoka, *Pharm. Res.* 9, 1235 (1992).
71. A. Lin, N. Slack, C. George, C. Samuel, C. R. Safinya, unpublished results.

What is claimed is:

1. A method for regulating the structure of a macromolecule-lipid complex comprising:
   a. selecting a charged macromolecule;
   b. selecting a charged lipid combination; the charge of the lipid combination being opposite of the charge of the macromolecule;
   c. determining an amount of the macromolecule and the lipid combination sufficient to regulate the structure of the complex by:
      i. selecting a characteristic or multiple characteristics of the complex from the group of characteristics consisting of macromolecule interaxial distance ($d_M$), membrane thickness of the lipid combination ($\delta_m$), and the ratio (L/D) between the weight of the lipid combination (L) and the weight of the macromolecule (D); and ii. modulating any of the characteristics not selected in (i) so as to achieve the selected characteristic thereby determining the amount of the macromolecule and lipid combination sufficient to regulate the structure of the complex; and d. combining the macromolecule with the lipid combination in the amount so determined thereby resulting in the complex having the desired structure.

2. A method for regulating the interaxial distance of adjacent macromolecules within a macromolecule-lipid complex comprising:

a. selecting a charged macromolecule;

b. selecting a charged lipid combination; the charge of the lipid combination being opposite of the charge of the macromolecule;

c. determining an amount of the macromolecule of (a) and the lipid combination of (b) sufficient to regulate the structure of the complex by:

i. selecting a desired macromolecule interaxial distance ($d_M$); and ii. modulating any of membrane thickness of the lipid combination ($\delta_M$), or the ratio (L/D) between the weight of the lipid combination (L) and the weight of the macromolecule (D) so as to achieve the desired macromolecule interaxial distance; and combining the macromolecule with the lipid combination in the amounts so determined so as to produce the complex having the desired structure.

3. A method for regulating the density of macromolecules within a macromolecule-lipid complex comprising:

a. selecting a charged macromolecule;

b. selecting a lipid combination; the charge of the lipid combination being opposite of the charge of the macromolecule;

c. determining an amount of the macromolecule of (a) and the lipid combination of (b) sufficient to regulate the structure of the complex by:

i. selecting a desired macromolecule density; and ii. modulating any of membrane thickness of the lipid combination ($\delta_M$), or the ratio (L/D) between the weight of the lipid combination (L) and the weight of the macromolecule (D) so as to achieve the desired macromolecule density, d. combining the macromolecule with the lipid combination in the amount so determined so as to produce the complex having the desired structure.

4. The method of claim 1, wherein the characteristic so selected from group is macromolecule interaxial distance or macromolecule density.

5. The method of claim 1, wherein the characteristics so selected from the group are macromolecule interaxial distance and macromolecule density.

6. The method of claim 1, 2, or 3, wherein modulating is effected using the formula: $d_M = (L/D)(A_M \rho_M)/(\delta_m \rho_L)$.

7. The method of claim 2, wherein the macromolecule is a charged macromolecule and the charge of the lipid combination is opposite of the charge of the macromolecule.

8. The method of claim 1, 2, or 3, wherein the macromolecule is a nucleic acid molecule.

9. The method of claim 1, 2, or 3, wherein the macromolecule is linear, circular, nicked circular or supercoiled.

10. The method of claim 9, wherein the nucleic acid molecule is a DNA or RNA.

11. The method of claim 2, 3, or 4, wherein the macromolecule is a peptide, protein polysaccharide, a combination of a protein and carbohydrate moiety.

12. The method of claim 1, 2, or 3, wherein the lipid combination comprises a neutral lipid component and a charged lipid component.

13. The method of claim 1, 2, or 3, wherein the lipid combination and the macromolecule are associated so as to form a complex in an isoelectric point state.

14. The method of claim 1, 2, or 3, wherein the lipid combination and the macromolecule are associated so as to form a complex in a positively charged state.

15. The method of claim 1, 2, or 3, wherein the lipid combination and the macromolecule are associated so as to form a complex in a negatively charged state.

16. The method of claim 12, wherein the neutral lipid is dioleoyl phosphatidyl choline (DOPC) or 1,2-dioleoyl-sn-glycero-3-phosphoethanolamine (DOPE).

17. The method of claim 12, wherein the charged lipid is 1,2-diacyl-3-trimethyl-ammoniumpropane (DOTAP).

18. The method of claim 1, 2, or 3, wherein the macromolecule-lipid complex is a multilamellar structure wherein the lipid combination forms alternating lipid bilayers and macromolecule monolayers.

19. The method of claim 1, 2, or 3, wherein the macromolecule-lipid complex forms either an inverted hexagonal complex phase or a regular hexagonal complex phase.

20. A macromolecule-lipid complex produced by the method of claim 1, 2, or 3.

21. The macromolecule-lipid complex of claim 20, wherein the macromolecule comprises:

i. a lipid combination having a charged lipid component and a neutral lipid component; and ii. a charged macromolecule;

the charge of the lipid combination being opposite of the charge of the macromolecule; the lipid and the macromolecule being associated so as to form a complex in an isoelectric point state, wherein lipid combination forms a bilayer membrane to which the charged macromolecules are associated in an isoelectric point state, wherein the relative amounts of the neutral lipid component relative to the charged lipid component generates the lipid bilayer membrane having a thickness of between 25 and 75 angstroms.

22. A macromolecule-lipid complex of claim 20, wherein the complex comprises:

i. a charged lipid combination; and ii. a charged macromolecule;

the charge of the lipid combination being opposite of the charge of the nucleic acid molecule; the lipid and the macromolecule being associated so as to form a complex in an isoelectric point state, wherein:

a. the lipids form a bilayer membrane to which the macromolecule is associated, wherein the relative amounts of the lipid components generate the lipid bilayer membrane having a thickness of between 25 and 75 angstroms; and b. the conformation of the complex has macromolecule exhibiting interaxial spacing of a range between 50 and 75 angstroms.

23. A method for transferring the macromolecule in the macromolecule-lipid complex of claim 20 to a cell comprising contacting the complex with the cell under sufficient conditions so that the macromolecule releases from the complex and transferring the macromolecule to the cell.

24. A lubricant composition comprising the macromolecule complex of claim 20 and an acceptable carrier.

25. The lubricant composition of claim 24, wherein the lubricant exhibits liquid crystalline properties.

26. A method for reducing friction between two surfaces comprising contacting the surfaces with the liquid lubricant of claim 24 so as to reduce friction between the two surfaces when the surfaces are put in contact.

27. A method for creating a pattern on a surface comprising applying the macromolecule-lipid complex of claim 20, on the surface thereby creating a pattern on the surface.

28. The method of claim 27, wherein the pattern is used to create a mask.

29. A method for creating a material having desired properties comprising:

a. applying a macromolecule-lipid complex to a surface by the method of claim 27;

b. applying the material onto the complex of (a), wherein the molecules self-assemble based on its interactions with the complex; and c. removing the complex from the surface thereby creating the material having a regulated structure.

30. The method of claim 29, wherein the complex is in a multilamellar, regular hexagonal, or inverted hexagonal phase.

31. The method of claim 29, wherein the material so created is a molecular sieve for separating molecules based on size.

\* \* \* \* \*